United States Patent [19]
Buckner et al.

[11] Patent Number: 6,089,864
[45] Date of Patent: Jul. 18, 2000

[54] BIO-FEEDBACK, DATA ACQUISITION TEETH GUARDS, METHODS OF THEIR MANUFACTURE AND USE

[75] Inventors: Randall R. Buckner; John D. Dees, both of Houston, Tex.; William L. Hintermister, 2330 Montgomery Park Blvd. #1035, Conroe, Tex. 77304

[73] Assignee: William L. Hintermister, Southport, N.C.

[21] Appl. No.: 09/243,340

[22] Filed: Feb. 1, 1999

Related U.S. Application Data

[63] Continuation-in-part of application No. 08/970,365, Nov. 14, 1997, abandoned
[60] Provisional application No. 60/030,977, Nov. 15, 1996.

[51] Int. Cl.[7] .................................................. A61C 9/00
[52] U.S. Cl. ............................... 433/71; 433/68; 433/6
[58] Field of Search .................................. 433/6, 24, 68, 433/71; 128/776, 777

[56] References Cited

U.S. PATENT DOCUMENTS

| | | | |
|---|---|---|---|
| 3,349,489 | 10/1967 | Shackelford | 433/68 X |
| 3,390,459 | 7/1968 | Seidenberg | 433/69 X |
| 4,592,727 | 6/1986 | Bloomfield | 433/71 |
| 4,976,618 | 12/1990 | Anderson | 433/72 X |
| 5,078,153 | 1/1992 | Nordlander et al. | 433/215 X |
| 5,458,487 | 10/1995 | Komatsu et al. | 433/71 |

*Primary Examiner*—Nicholas D. Lucchesi
*Attorney, Agent, or Firm*—Robert W. Strozier

[57] ABSTRACT

A diagnostic and therapeutic apparatus for use in the evaluation, detection, and treatment of humans that suffer from chronic grinding of the teeth known as "bruxing." The apparatus includes a pressure sensor contained in a mouth piece and electronic for detecting activation of the sensor due to bruxing and for generating an human cognizable output in response to bruxing. The apparatus can also include electronics for storing and analyzing human bruxing activities.

27 Claims, 24 Drawing Sheets

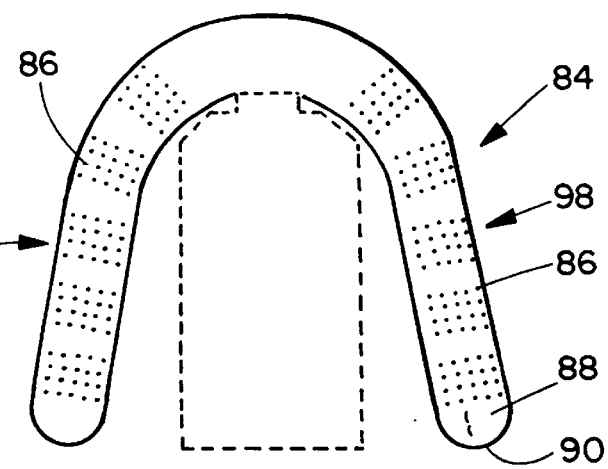
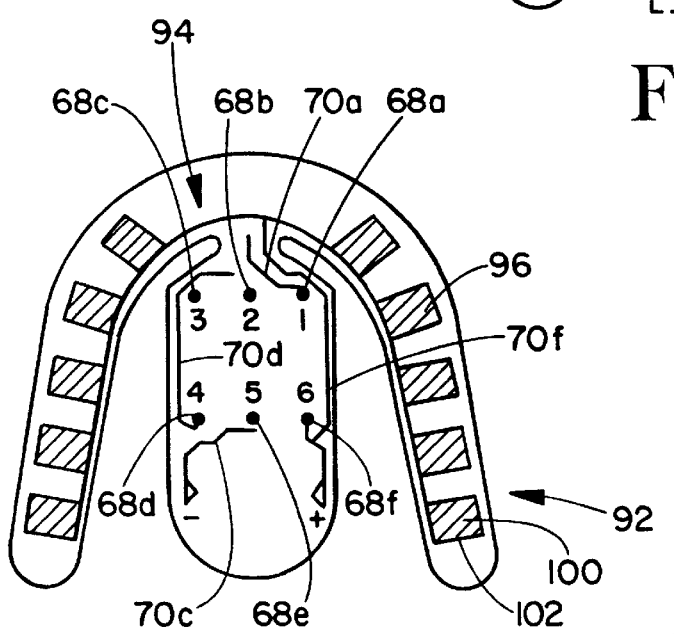
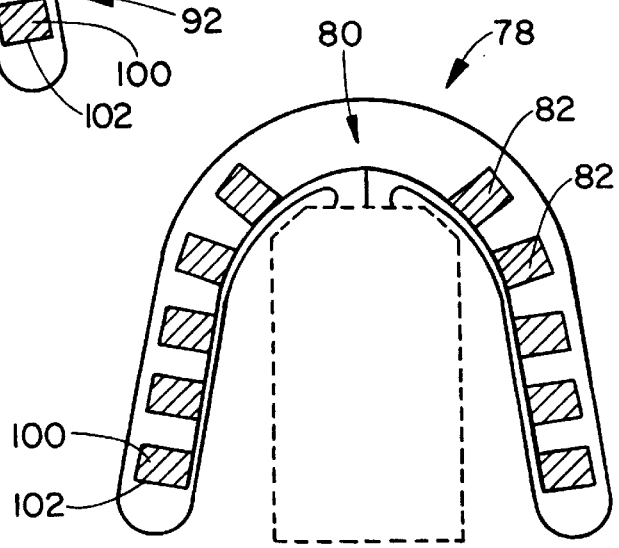
Fig. 5a
Fig. 5b
Fig. 5c

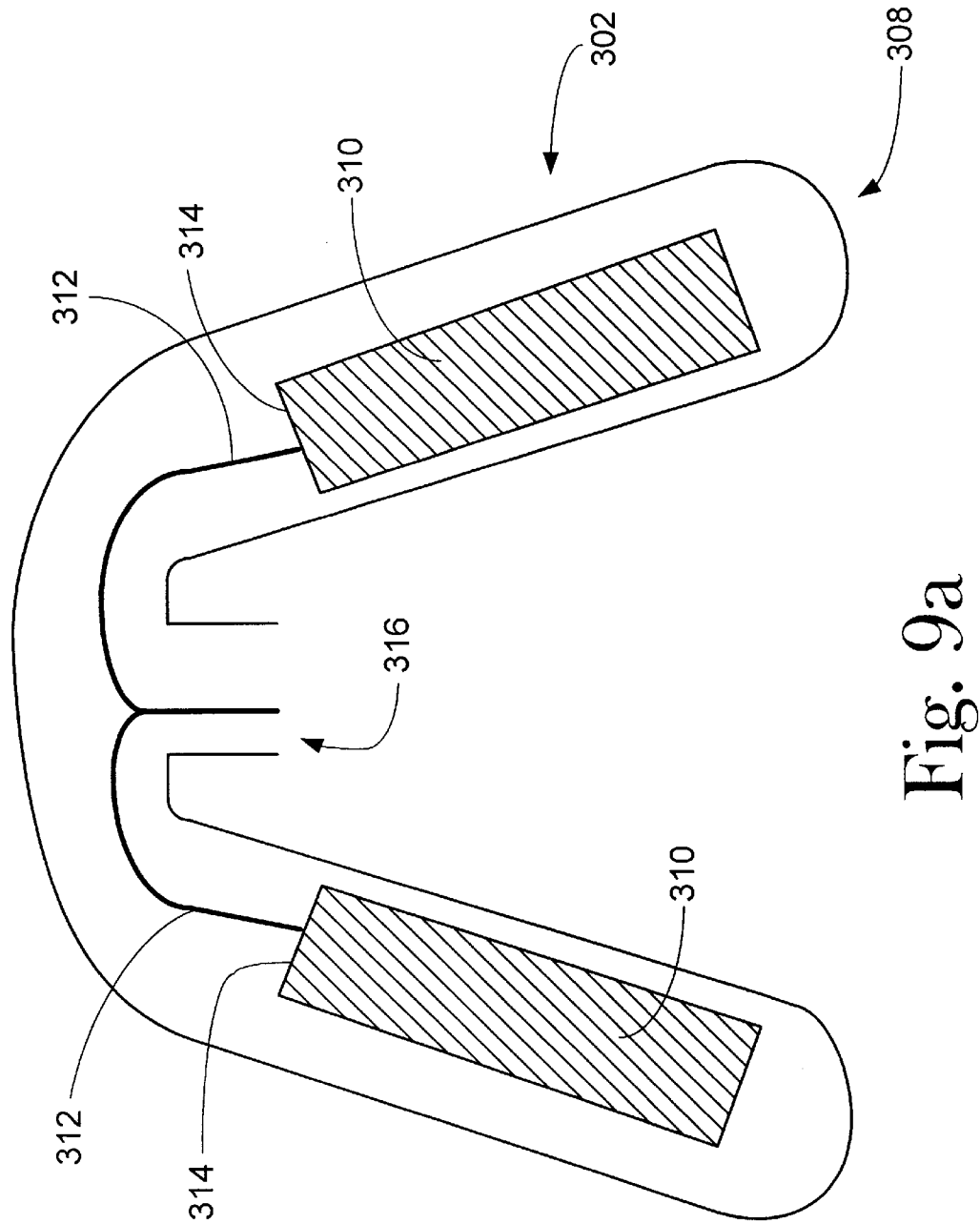

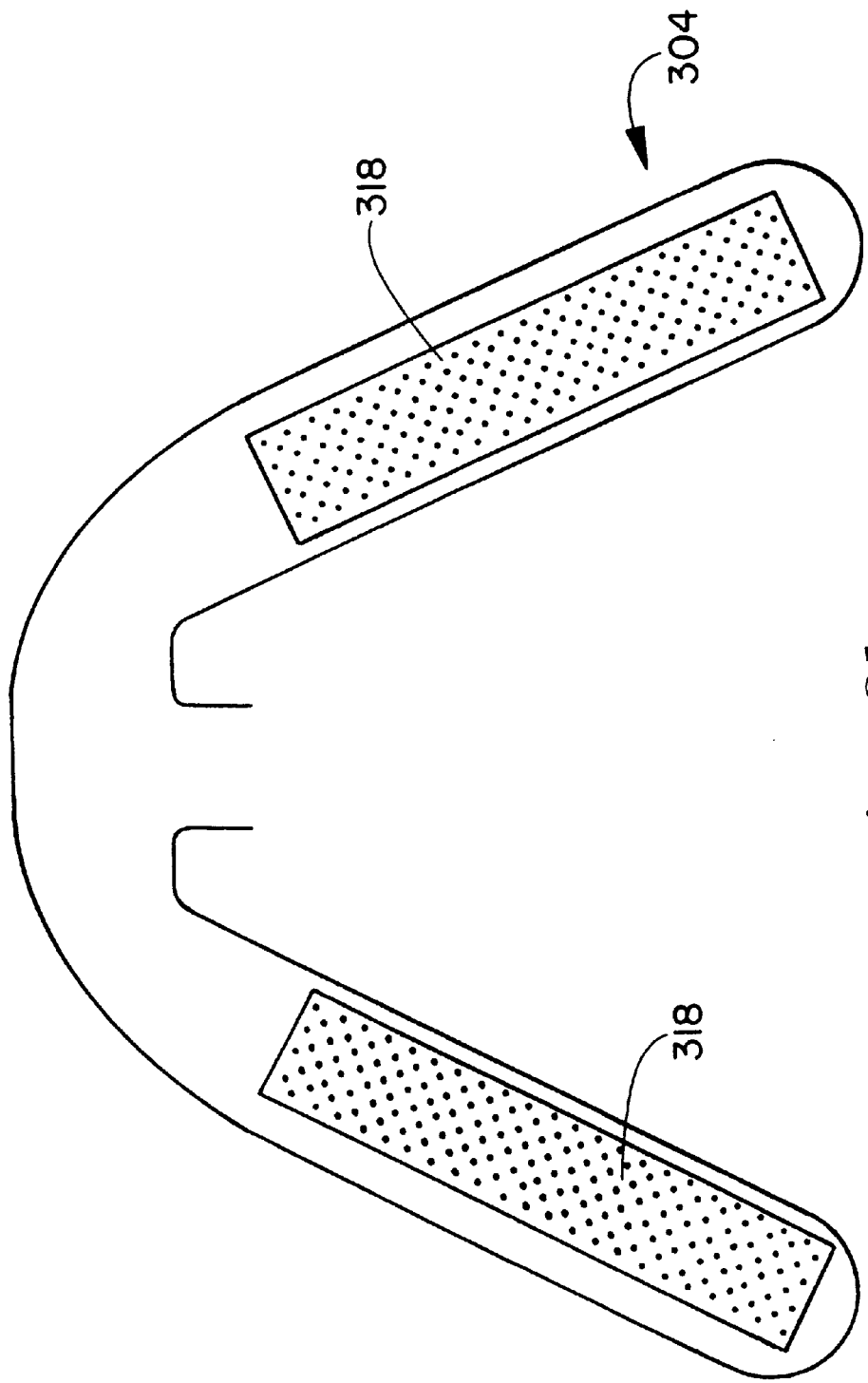

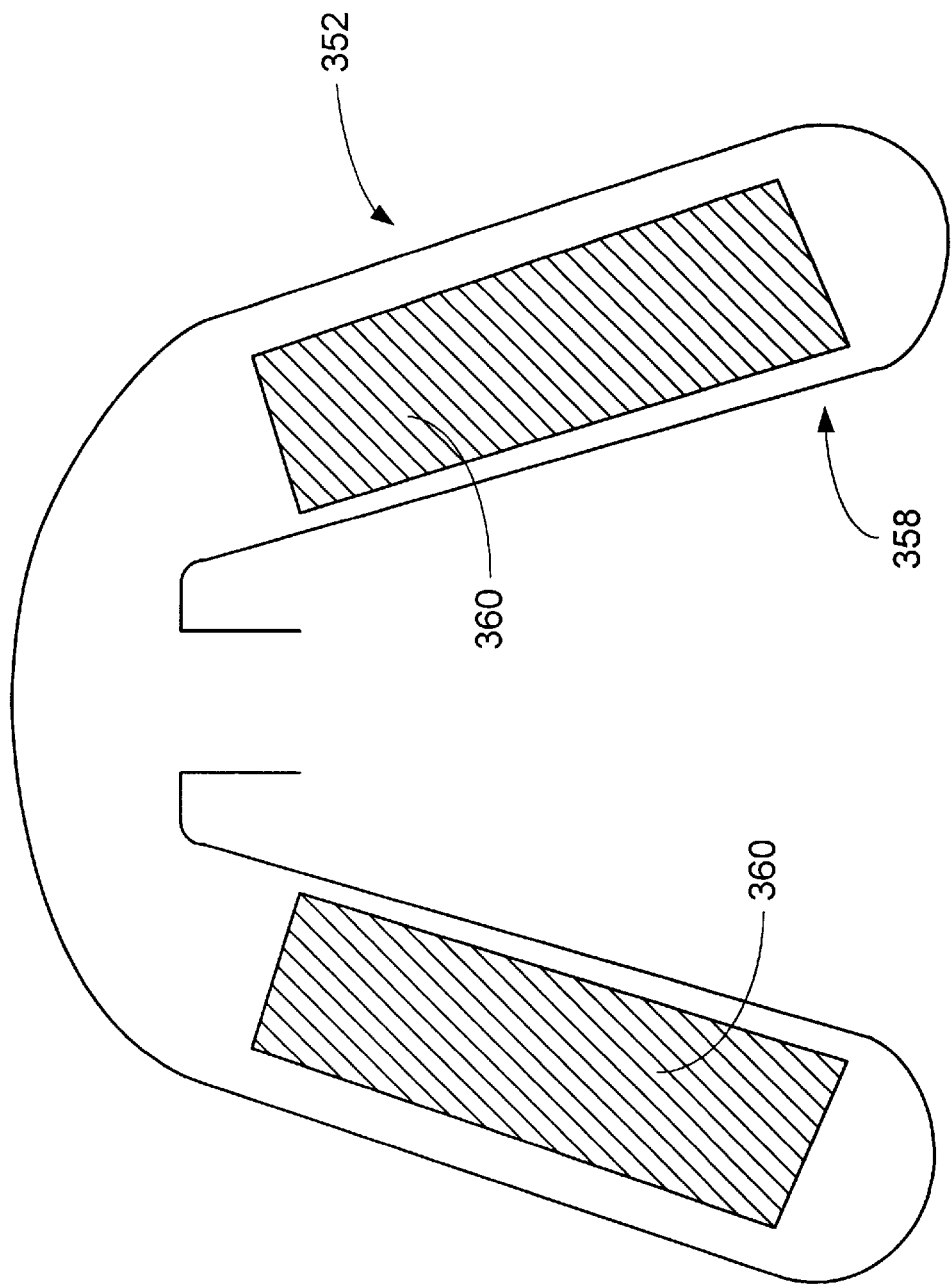

BIO-FEEDBACK, DATA ACQUISITION TEETH GUARDS, METHODS OF THEIR MANUFACTURE AND USE

RELATED PATENT APPLICATIONS

This application is a continuation-in-part of U.S. patent application Ser. No. 08/970,365, filed on Nov. 14, 1997 now abandoned, which claims priority of U.S. provisional patent application Ser. No. 60/030,977 filed on Nov. 15, 1996.

BACKGROUND OF THE INVENTION

1. Field of the Invention

This invention relates generally to devices to be worn to prevent teeth and/or jaw damage caused by "grinding of the teeth" sometimes also known as bruxing, TMJ, clinching, gritting, or other related psychological and physiological conditions and to methods for behavior modification of such condition and to methods for acquiring data associated with such conditions.

More particularly, this invention relates to mouth pieces or teeth guards to prevent grinding of teeth and to provide bio-feed back and data acquisition capabilities by incorporating in teeth contacting regions of the guard, pressure sensing devices in electrical communication with an integrated circuit device capable of monitoring the sensing devices and transmitting a signal when a change in a normal pressure state of the pressure devices occurs to a receiving device capable of invoking a human cognizable response designed to indicate to the wearer when teeth grinding is occurring and/or to collect, store and/or analyze data associated with grinding episodes.

2. Background Information and Description of the Related Art

In prior art, the only tool that a dental doctor has now available for handling patients that grind their teeth during sleep is a simple device known as a mouth piece, split, teeth guard or mouth guard that is molded out of a hard or soft polymer conforming to a patients upper palate and teeth or lower jaw and teeth. This device offers no ability to do diagnosis or therapy towards a cure. It's only function is to protect a sufferer from damaging the enamel that will eventually deteriorate from the hard pressure and friction occurring during bouts of tooth grinding.

Thus, there is a need in the art for a device that not only protects the teeth or the enamel of the teeth and/or jaw from damage during bruxing episodes, but also provides information that can be used either to study teeth grinding or augment a patient's behavior to reduce and/or eliminate bruxing episodes.

SUMMARY OF THE INVENTION

The present invention provides mouth piece or teeth guard devices that include a flexurally resilient mouth member designed to detachably engage a portion of or all of the teeth of a wearer's upper or lower jaw to prevent tooth damage during teeth grinding episodes. The mouth member includes at least one pressure sensing device incorporated into at least one tooth socket or region thereof. The region is selected so that the pressure sensors become interposed between teeth during grinding episodes. The sensors are in electrical communication with electronic devices capable of monitoring and generating an action signal in response to a change in a state of the pressure sensing devices which signifies a teeth grinding episode and optionally capable of collecting, processing and/or storing information about each grinding episode.

The present invention also provides a mouth piece, mouth guard or teeth guard as described above coupled with a receiving device capable of receiving the action signal from the mouth piece, mouth guard or teeth guard and generating a cognizable bio-feed back output in response to each grinding episode at either a conscious or subliminal level, i.e., if the wearer is asleep, the output can either wake the wearer up or generate an output that can be sensed by the brain without waking the wearer up, while if the wearer is awake, the output such must be sufficient to cognizable to the wearer.

The present invention further provides mouth piece, mouth guard or teeth guard devices as described above coupled with a data acquisition device capable of receiving the transmitted signal from the mouth piece, mouth guard or teeth guard and either dynamically, periodically or upon user demand analyze information contained in the signal or derived from the signal, including the frequency and duration of each grinding episode and optionally a pressure pattern and/or intensity pattern associated with each grinding episode.

This invention further provides for mouth piece, mouth guard or teeth guard devices as described above incorporating both a device capable of rendering a bio-feed back response and a device capable of collecting and storing of data contained in the transmitted signal from the mouth piece, mouth guard or teeth guard device.

This invention also provides methods for augmenting teeth grinding habits including placing in the mouth of a user a mouth piece, mouth guard or teeth guard as described above, transmitting a signal produced in response to a change in a state of the pressure sensors, receiving the signal from the mouth piece, mouth guard or teeth guard and generating a user cognizable response to each grinding episode sufficient to make the user aware of the episode either consciously or subliminally.

This invention further provides methods for acquiring data regarding teeth grinding habits including placing in the mouth of a user a mouth piece, mouth guard or teeth guard as described above, transmitting a signal produced in response to a change in a state of the pressure sensors, receiving the signal from the mouth piece, mouth guard or teeth guard in a data storage device and storing data contained in the signal in the device corresponding to a set of properties of each grinding episode.

The previous two methods can also be combined to provide a method for data acquisition and bio-feed back.

The present invention also provides methods for making mouth guards with pressure sensors contained therein and associated electronics and methods for making the bio-feed back and data acquisition systems utilizing the mouth guards of the present invention.

This invention further provides a new membrane pressure sensing device and methods for making and including the devices in mouth pieces.

Thus, one aspect of this invention is to provide apparatus designed to diagnose and/or collect information about the human problems associated with grinding of teeth during sleep. Another aspect is to use such devices to treat the teeth grinding towards a cure. Another aspect of this invention is to provide methods for manufacturing mouth guards comprising plastic laminants having pressure sensors, radio transmitters and associated electronics contained therein and methods for fitting such devices to a human mouth.

The present invention further provides an mouth guard including an outer layer conforming substantially to the shape of an upper teeth and pallet outline of a person having a top substantially conforming to the upper teeth and pallet or roof of the mouth of the person and a bottom which is relatively smooth and designed to engage the teeth of a lower jaw. The mouth guard further includes sensing layer contained within the outer layer where the sensing layer includes a plurality of metal dome switches distributed along a molar region of the mouth guard in electrical communication with electronics located in the pallet region of the guard and also contained within the outer layer of the guard. The switches are design to be in an OFF condition (open circuit condition) when no force is applied between the top and bottom of the outer layer of the guard and to be in a ON condition (closed circuit condition) when a force sufficient to overcome a force rating of each switch. The electronic includes a battery, an integrated circuit and electric wires connecting the battery, IC and switches. The IC includes a transmitter and the electric wiring includes an antenna.

The present invention further provides an mouth guard including an outer layer conforming substantially to the shape of an upper teeth and pallet outline of a person having a top substantially conforming to the upper teeth and pallet or roof of the mouth of the person and a bottom which is relatively smooth and designed to engage the teeth of a lower jaw. The mouth guard further includes sensing layer contained within the outer layer where the sensing layer is a membrane switch including a top layer, a middle layer and a bottom layer. The top layer includes a conductive area and wires extending from the conductive area. The middle layer includes a plurality of perforations arranged in regular or irregular patterns. The bottom layer includes a conductive area and wires extending from the conductive area where the bottom layer conductive area conforms substantially to the top layer conductive area. The membrane switch is design to be in an OFF condition (open circuit condition) when no force is applied between the top and bottom of the outer layer of the guard and to be in a ON condition (closed circuit condition) when a force sufficient to overcome a force rating of switch. The electronic includes a battery, an integrated circuit and electric wires connecting the battery, IC and switches. The IC include a transmitter and the electric wiring includes an antenna.

The present invention also includes a battery-less mouth guard where everything save the battery can be any one of the embodiments described above or any combination thereof and where the power needed to transmit a signal is obtained from an energy field which microelectronic circuits, preferably mounted in the pallet area of the device and antenna following the front outer contour of the guard, capable of being energized or extracting energy from the field. The energy is then used by the mouth guard to transmit a signal whenever the sensing layer within the mouth guard changes state indicating sufficient force being applied across the sensing layer to change the state of the circuit (open to closed). The change in state closes circuits in the electronic circuitry of the mouth guard allowing the circuitry to be energized by the energy field resulting in signal generation and transmission to a receiver. Of course, the wearer must be within the active zone of the energy field for the battery-less unit to work. Thus, the energy field generator should be located in a bedroom of the wearer sufficiently close to the bed so that when the circuitry in the guard closes due to a bruxing episode of sufficient force to change the sensing device from an open state to a closed state, the device will be able to extract energy from the field, generate and transmit a signal evidencing the change in state of the pressure sensing device within the guard.

DESCRIPTION OF THE DRAWINGS

The invention can be better understood with reference to the following detailed description together with the appended illustrative drawings in which like elements are numbered the same:

FIG. 5a is a top view of the perforated film of the membrane of FIG. 3;

FIG. 5b is a top view of the bottom film and associated circuitry of the membrane of FIG. 3;

FIG. 5c is a top view of the top film and associated circuitry of the membrane of FIG. 3;

FIGS. 9a–c is a second embodiment of a second type of membrane switch of this invention;

FIGS. 10a–c is a third embodiment of a second type of membrane switch of this invention;

DETAILED DESCRIPTION OF THE INVENTION

Figure 1A:
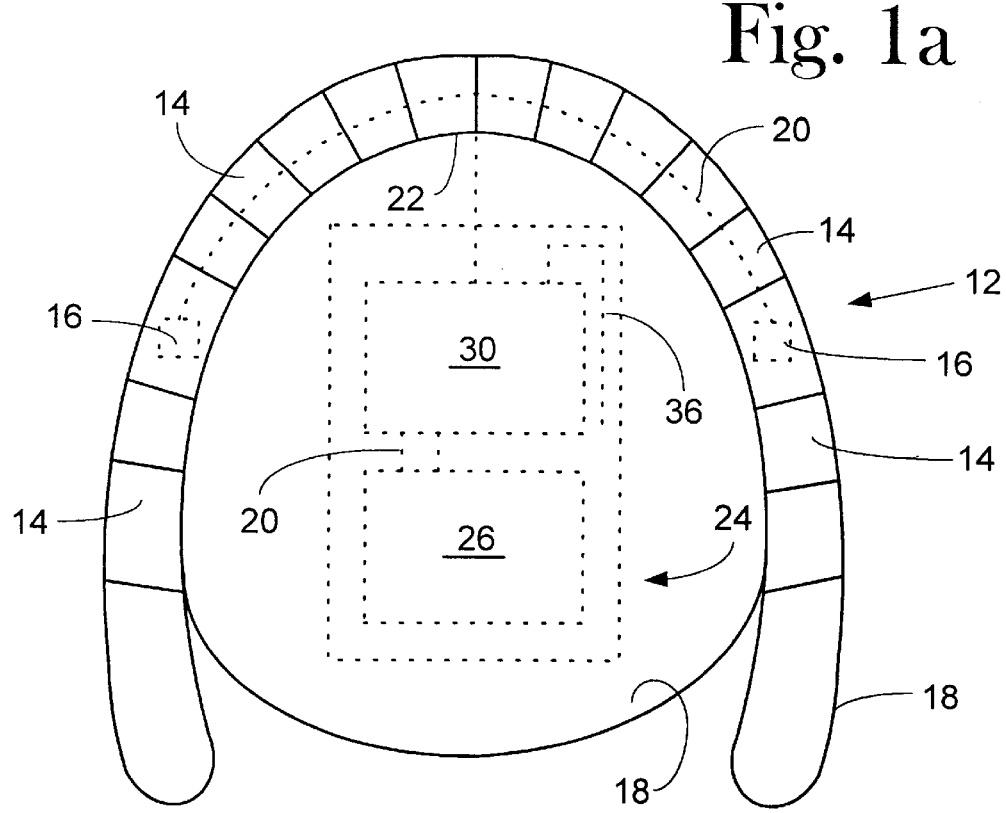
FIGS. 1a–c are a top schematic view, side view of a mouth guard and a top view of a receiver unit of the present invention.

The inventors have found that an apparatus can be constructed that incorporates into a mouth guard or piece at least one pressure sensor in electric communication with an electronic device capable of monitoring the pressure sensor(s) and transmitting a signal when a state of one sensor or a plurality of sensors changes in response to a teeth grinding episode. Besides simply signifying whether the monitored state has changed, the transmitted signal can optionally include data indicating which sensors have changed state, the pressure amplitude experienced by each activated sensor, and/or a direction perpendicular to an applied force.

The inventors have also found that the mouth piece containing pressure sensors and a transmitter can be coupled with a receiver unit that is capable of receiving the transmitted signal from the mouth piece or guard and generating a human cognizable response such as a sound, vibration, pressure contact, electrical stimulus, taste and/or smell stimulus other cognizable sensory output or combinations thereof. The cognizable response can cause a wearer or user to become conscious of the fact that he/she is grinding his/her teeth or preferably, the response is designed to cause a subliminal recognition of the onset of a grinding episode. The response is designed to induce a behavioral recognition of the onset and cessation of a grinding episode and potentially induce a behavioral modification of a grinding habit to either reduce or eliminate this potential dental damaging habit.

The inventors have also found that the transmitting mouth guard can also be coupled to a data acquisition system capable of receiving the transmitted signal and storing the information contained in the signal so that the frequency of episodes and other properties of each grinding episode can be stored for dynamic or subsequent analysis.

One embodiment of the present invention includes, an improved dental mouth piece that helps protect the wearer's teeth against the harmful effects of daytime or nighttime bruxing (forceful grinding and clinching of the teeth) and helps minimize the frequency and intensity of the bruxing. In addition to the standard, molded plastic dental nightguard that is custom fit and slips snugly onto and covers the upper or lower teeth, this improved guard contains electronics that give instant feedback by alerting the wearer when he/she begins to brux. When the wearer begins to brux these electronics consisting of a pressure activated switch, radio frequency transmitter and battery power source sends a radio signal to a wrist alarm which alerts the wearer. When the wearer stops bruxing, the alarm stops automatically.

The mouth guard can be constructed of any plastic material, laminant material or composite material. Such material include, without limitation, polystyrene, elastomers such as polybutadiene, styrene-butadiene copolymers, natural rubber, or the like, thermoplastic elastomers such as SBS, SIS or similar thermoplastic elastomers, polyesters, polyacrylates and/or acrylics, polyurethanes, polyamides, polyolefins, polylactones, or the like or mixtures or combinations thereof. Suitable materials also include any material currently used to make mouth pieces. These materials can be used in either a cured or uncured state for those material that can be chemically or radiation cured. Preferably, the materials used on the exterior surfaces of the mouth pieces of the present invention are Food and Drug Administration approved for use in the mouth. The mouth piece or guard is preferably constructed of a flexurally resilient material so that the mouth piece can undergo repeated grinding episodes without significant loss of integrity or flexible fatigue.

The pressure sensors are generally incorporated into regions of the mouth guard that become interposed between teeth in an upper jaw and lower jaw of a wearer during a grinding episode. The sensors can be simple pressure activated on/off switches such as membrane switches and/or devises such as a load cell, strain gauge and/or polymeric membrane pressure gauges (elastomer switches) which generate an output signal proportional to either a magnitude and/or a magnitude and a direction of forces experienced by the pressure sensor during a grinding episode.

The monitoring and transmitting device is generally a chip having processing capabilities sufficient to monitor and determine a change in pressure state of at least one pressure sensor and to transmit a signal when a change in the state of one or more pressure sensors occurs. The device can either transmit a continuous signal (persistent signal) until a normal state is restored in the activated pressure sensors, transmit an intermittent signal while a sensor is in an activated or non-normal state or generate a start signal and a stop signal marking the start of a grinding episode and the stop of the episode.

If the pressure sensors are capable of monitoring amplitude and/or direction of applied forces, then the transmission is preferably continuous, but interment signals with amplitude and/or directional information averaged over duration of the interment signal or un-averaged can also be used.

Besides using a transmitter located in the mouth piece and a separate unit to generate an human cognizable output, the mouth piece itself can include a electronic and mechanical unit that generates an output directly into the wearer's mouth. Such units could include vibratory devices such as peizoelectric transducers, other harmonic oscillating devices or other devices that can vibrate. The vibrations can be direct upward to the palate or downward to the tongue or to both the palate and the tongue.

The output unit could also be a device that administers a small the cognizable electric stimulus or shock. Additionally, the unit could be release a chemical agent that would either stimulate smell, taste or a combination thereof. Moreover, the mouth piece devices of this invention can include any combination of output devices both in the mouth piece and external to the mouth piece.

Furthermore, the data collection, processing and storage hardware and software could be all located in the mouth piece where the mouth piece can be removed from the mouth and the collected data downloaded from the device into an external data analysis unit.

One preferred embodiment of the night mouth guard of the present invention broadly includes the following three basic components:

One embodiment of the battery-less guard utilizes a power oscillator which produces ultra high frequency short wave energy from an associated antenna. An antenna in the guard is tuned to receive this signal and circuitry in the mouth guard is designed to extract energy from the energy from the power oscillator when the sensing circuit is closed to generate and transmit a signal evidencing a bruxing episode. Such systems power oscillator and receiver circuits are more fully disclosed in U.S. Pat. Nos. 4,288,689, 4,532, 511 and 5,019,815, incorporated herein by reference.

Other embodiments of the battery-less guard utilize electric and magnetic energy fields and antennas and circuitry in the mouth guard capable to extracting energy from such fields and using that extracted energy to generate and transmit a signal when the sensing device in the mouth guard is activated (changes to a closed condition) during a bruxing episode. Further information about these energy field generating systems and the circuitry effective in extracting energy therefrom is disclosed in U.S. Pat. Nos. 5,733,313, 5,140,263, 5,283,400 and 5,019,815, incorporated herein by reference.

In all of these embodiments utilizing energy fields to supply the required energy to the guard electronic when the sensing device is in a closed circuit state, once a signal from the mouth guard is generated and transmitted, a receiver capable of receiving the signal then generated a bio-feed back response to the wearer and/or records and stores the transmitted signal. The stored data can include start/stop information, duration information, power information and other information contained in the signal.

Section I

A plastic horseshoe shaped dental night mouth guard worn on the upper or lower teeth, preferably the upper teeth. It is made of plastic custom molded to the wearer's mouth and each individual tooth. Positioned inside the molded nightguard and lying flush with the biting surface of one or more teeth are one or more elastomer switches. (These elastomer switches and the electrical wires running from them are covered with a layer of flexible plastic and hermetically sealed therein such as those available from Elastomer Technologies, Philadelphia, Pa.). The wires running from the elastomer switches pass through a rear wall of the night mouth guard and into a central region located in a palette region of a wearer's mouth where electronics for monitoring the switches and transmitting a signal corresponding to the state of the switches are located.

Section II

A molded plastic and hermetically sealed compartment located in the concave space created by the horseshoe shape of the night mouth guard. This compartment is molded to and firmly attached to the rear wall of the horseshoe shaped night mouth guard. Inside this compartment is a cordless radio transmitter and battery power source. When the wearer begins to brux, the elastomer switch is depressed causing it to activate the transmitter which sends a radio signal to a receiving unit.

Section III

A wrist alarm or any other receiving unit is designed to receive the signal transmitted by the mouth device. The wrist alarm employs an audio and/or vibration alarm option which alerts the wearer the moment bruxing begins. (The elastomer switch is a toggle so the alarm activating signal is only sent for as long as the switch is depressed by the bruxing pressure). The moment the wearer stops bruxing, the signal stops and the alarm ends until the next grinding episode.

How to Use

Prior to going to sleep the wearer will insert the Dental Nightguard with Biofeedback into his/her mouth and slip it over the upper teeth where it will remain for the night. The wearer will then strap on the wrist alarm and turn the wrist alarm power switch to on. Upon waking at the end of the night, the wearer will turn the wrist alarm power switch off and remove the mouth guard from the mouth. Of course, the device of the present invention can be worn during the day to act as a bio-feed back unit or as a data acquisition system to study teeth grinding during work.

Although the mouth guard can incorporate any type of pressure sensor, the inventors have found that a preferred sensor is a membrane having at least one pressure sensing region or switch embedded between two mouth compatible plastic or rubber sheets in at least on tooth socket or cavity in the mouth guard.

Moreover, the electronic units and battery can be located in other regions of the mouth piece than in the palate region of the mouth. The electronic could be located in areas of the mouth piece that extend up onto the side of the teeth and up onto the gum. Further more, any other power supply can be used provided that the supply mechanism generates sufficient power for night time or day time monitoring. The power supplies can also be rechargeable.

Preparation of a Membrane Switch of This Invention

Prior art uses of polyamides including caprolactam polyamides such as Kapton sold by the DuPont company under the trade name PYRALUX®, have been primarily for single and multi layered flexible circuitry in the telecommunications industry for such devices as small, portable phones and wirelines used in the oil industry. There are well established procedures for using these polyamide materials to incorporate metal circuitry in a polyamide laminant.

The inventors have found that these polyamide materials can be used to form flexible pressure sensing switches or detectors. The pressure switches are designed to be laminated between two acrylic sheets or similar plastic materials so that the switch is in a normal open or off state until pressure is applied to the laminant sufficient to cause the switches to change to a closed or on state. The acrylic sheets generally have a thickness between about 0.005 and about 0.10 inches, with thicknesses between about 0.010 and about 0.08 being preferred and thicknesses between about 0.020 and about 0.060 being particularly preferred.

The membrane switch of the present invention includes a perforated insulating layer interposed between two sheets of polyamide material with conductive circuitry on their sides that contact the perforated insulating layer. The perforations are preferably patterned to coincide with conductive mesh patterns associated with the conductive circuitry. Although any conductive material can be used preferred conductive materials include conductive metals such as the noble or group VIII metals, the group 1b metals, including gold, silver, platinum, palladium, iridium, rhodium, copper or the like. Besides metals, conductive polymers can be used as well.

Material Requirements

The process for making the membrane switches of the present invention utilizes the following materials: (a) two 12"×12" sheets of single-sided copper clad polyamide where the copper is of a thickness is equal to about one once of copper per square foot of polyamide film. It should be recognized that any sheet size can be used to make the membrane switches of this invention as is well-known in the art. One preferred copper clad film is sold by the DuPont company under the trade name PYRALUX LF9110. The polyamide film is about 0.001 inches thick; (b) one 12"×12" sheet of polyamide sandwiched between two adhesive layers. The film thickness is about 0.001 inches and the adhesive layers are about 0.001 inches thick. One preferred adhesive polyamide sheet is sold by the DuPont company under the trade name PYRALUX LF0111.

Tooling

The process is performed using the following tooling: All etched images and corresponding perforated core membrane must have common mechanical reference points outside the final useable area for registering the 3 different sheets when "booking-up" for pressing together in the lamination process. Photoplotted Mylar® positives of computer aided design images of a top circuit layer and bottom circuit layer must be made with registration of all desired images, (number of individual units desired), all stepped and repeated precisely. Registration targets for tooling pins must have been added outside the usable area in the periphery of the film. These targets must be common to all sheets of plotted films and the "XY" coordinate list that will be used to drill or punch the same locations in the periphery of the actual film sheets to be used in manufacturing. A "drill file" or ascii readable list of the tooling targets is saved for use in the manufacturer's machining department.

Processing

The process includes preparing as follows: (a) lay the two sheets of copper clad polyamide film or sheet material with the copper surface directed toward each other with the adhesively coated polyamide sheet interposed there between. These three films or sheets are then sandwiched between two sheets of "backup-material, " which is generally a hard material such as pressed board or Masonite with smooth, flat coplanar top and bottom surfaces as is well-known in the art. The construct is then pinned together to form a "book" that can then be held in place on a precision drilling machine commonly referred to as a computerized numerically controlled (CNC) drilling machine as is well-known in the art.

The machine is then loaded with coordinates that correspond to the common reference targets (tooling holes). The drilling operation is conducted at a feed and speed rate the will cut and remove portions of the films or sheets of polymeric material without tearing or smearing the materials. The target holes have a diameter that corresponds to common pin diameters including without limitation pin sized of 0.125, 0.156, 0.187 or 0.250 inches or combination thereof.

After the tooling holes are drilled, the book is taken apart and the two metal clad films or sheets are set aside. Using common tooling practices, the CNC machine is loaded with the information needed to drill holes in the interposed insulator sheet or film to form the perforated interposed, insulator sheet or film. The interposed film is then remounted on the CNC machine sandwiched between two slip sheets generally made of Teflon. An entry material such as a metal plate or film is then placed on top of the sandwich interposed layer such as an aluminum "entry" material. Holes are then drilled in the mounted interposed, insulator sheet placing holes or perforations in a desired pattern derived from the CAD design of the final membrane switch which contains the information for constructing the membrane switch from its constituent parts. Once the perforations or holes have been drilled in the interposed, insulator sheet, the sheet is removed from the machine or breakdown of the book occurs and the sheet is set aside.

Printing Circuits

With the perforated film prepared, the printed circuits on each metal clad film is constructed. The process of forming the circuitry on the metal clad circuit sheets generally includes first cleaning the metal surface as is well-known the art in preparation for applying a photo-resist. The photo-resist can be any photo-resist used in the art, provided that the photo-resist is compatible with the metal making up the cladding such as photo-resistive inks or laminated films. One preferred laminated film is the Riston 200 series of dry films from the DuPont company. In addition, any other technique for forming circuitry on the surface of polymeric materials form can be used as well as other type of polymers as is well known in the art.

The photo-resist in then applied to the cleaned metal surface. A photoplotted film or mask which have transparent and opaque areas corresponding either to a positive or a negative image of the desired circuitry is then aligned with the registration targets and tooling holes that are drilled on the material. The masked, photo-resist coated metal clad sheet is then exposed to a high intensity UV light using a so called contact camera for a duration prescribed for the particular photo-resist being used to form a photo-cured pre-circuit sheet. The UV light cures the photo-resist exposed to the light, leaving the unexposed photo-resist uncured. The photo-cured film is then developed to remove uncured or unexposed photo-resist leaving the corresponding metal surface unprotected. In the preferred process, the portions of the metal surface having the cured photo-resist thereon will become the circuitry and the unprotected or exposed portion of the metal surface will be removed.

Once the uncured photo-resist has been removed and the corresponding metal surface exposed, the developed sheet is optionally visually inspected to ensure the integrity of the cured photo-resist. The sheet is then subjected to an etching process that will remove the exposed portions of the metal surface. Any etching process known in the art could be used in the practice of this invention. Such etching processes include a dip or spray etch commonly referred to as the "Peroxy-Sulfuric" process or the "Alkaline Ammoniacal" spray etch. Either process is acceptable with proper neutralization and rinsing after etching; however, one of ordinary skill would recognize the polyamides can degrade in the presence of highly alkaline solutions which can cause a swelling of the material, if the material is not properly cleaned afterwards.

After etching, the circuit sheets are cleaned and rinsed thoroughly. The clean sheets are then dried, preferably in a convection oven at a temperature preferably not exceeding about 200° F. for a time not to exceed about 30 minutes. However, other temperatures and times can be used provided that the film is not damaged or degraded by the thermal history (temperature and time). After drying, the material is allowed to stress relieve for a period of about 3 hours at room temperature in a clean, low humidity area. The period of stress relief is not critical, but should be sufficient to allow the film and metal thereon to come to a new equilibrium state. Of course, the top and bottom sheet circuitry is not the same so each sheet will have its own photomask associated therewith producing the circuitry intended for that sheet.

Lamination

When making small quantities of the membrane switches of this invention, windows or areas that are to be removed from the top metal clad sheet and from the perforated sheet to expose the portions of the circuitry of the bottom layer or sheet can be removed by any method known in the art including, without limitation, cutting away the windows or areas by hand using an X-Acto knife or other surgically clean and sharp instrument. The "membrane" layer (perforated sheet) is cut away approximately 0.075 inches higher than the top circuitry containing layer. This is to expose one of the circuits of the Top to overlay and touch one of the circuits on the Bottom that corresponds to it on the design. These circuits are, eventually during the final assembly process, joined by a small bead of Tin-Lead solder to give continuity to this essential circuit. When making larger quantities of the membrane switches of this invention, the window cutting step is generally performed with a steel-ruled die for more accurate and quick removal.

Using pins corresponding in diameter to the tooling holes previously drilled in the materials, lay in order first the bottom circuit layer, copper circuits side up, next, the middle membrane material with any and all protective sheeting applied during raw manufacturing removed, and finally the top circuit layer, copper circuits side down. With the materials firmly held by the pins in registration, the pre-laminant is tacked down in several places along its edge to hold it together with a hot soldering pencil or other tacking device. Hold the pencil down against the material in each tack spot for a duration of approximately 10 seconds at a temperature of about 500° F. Tacking melts the adhesive on the top and bottom of the middle or perforated membrane layer and bonds the 3 pieces, (sheets of material) so they cannot become mis-registered in the final process to form a pre-laminated membrane switch sheet.

Using a common art "Laminating Press" (such as ones used normally for making multilayered printed circuit boards), the laminating process generally uses "press plates", "separator plates", and Teflon release sheets such as "Tedlar" or "Pacothane." Book up the press fixture in the following order: (a) a 0.250 inch bottom press plate preferably steel; (b) a bottom press pad or driving medium such as "Kraft" paper in multiple sheets or thermally resistive rubber sheet or specifically manufactured materials for this use such as "PacoPad" or "Isolam;" (c) a bottom stainless steel separator plate with IPC approved smoothness, polish, and co-planarity; (d) a teflon release sheet;"(e) the pre-laminated membrane switch sheet; (f) a teflon release sheet; (g) a top stainless steel separator plate; (h) a top press pad similar to the bottom press pad (b); and (i) a 0.250 inch top press plate similar to the bottom press plate (a).

It should be recognized that this method of booking is a departure from the norm of prior art. Usually, the press pads (driving medium) are used between every (c) and (d), and (f) and (g). This is to make the soft adhesive and plastic cores of the top and bottom layers of flexible circuits conform to and around any copper areas thereby sealing them more completely. This would not be a desirable effect in the membrane switch of this invention, because there are purposeful gaps created for the eventual pressing together (when the units are functioning as a switch) of the top and bottom copper circuits.

Using the normal 0.187 inch press pins that are used in printed circuit lamination, pin the entire book together in the middle of all four sides. Prior art uses this system and all constituents of the book are normally machined to register together this way. Place the book in a "Laminating Press" that has been preheated to about 360° F. and immediately apply a pressure about 250 psig. Since most Laminating Presses measure pressure in tons; for a 12 inch by 12 inch panel of membrane switches of this invention, the pressure corresponds to 18 tons.

When the book comes to full heat in the area of the membrane switches, it should stay under continual pressure for about 90 minutes. A set heat timer or program should shut off heating and maintain the laminate under pressure until the membrane switches or laminate cool down to a nominal 125° F.

After the press opens, take the book apart and remove panels of the laminated membrane includes a plurality of switch regions. Allow the laminated membrane to stress relieve for about 12 hours at room temperature while lying flat before any further use is made of the membrane such as assembly into a mouth piece. Of course, again, the time and temperature utilized for stress relief of the membrane can be other than 12 hours at room temperature provided that the temperature history does not adversely affect the membrane switch of this invention.

Although a preferred method for making the membrane switches of the present invention has been described above, any other method known in that art can also be used provided that the membrane switch can be activated by the pressures normally experienced in a grinding episode. Regardless of the type of pressure sensor used, the activation pressure for on/off type switch is preferably not set so low that incidental clinching of the teeth will not cause the pressure sensor to turn on. Preferably, the on pressure is between about 1 and about 50 psi, particularly between about 5 and about 50 psi and especially between about 10 and 50 psi. However, lower or high on pressures can be used and for mouth pieces for small children the ranges may be lower. For sensors that produce signal proportional to the magnitude of the applied force regardless of the magnitude of the force, the electronic preferably is designed with a pressure threshold signal intensity below which no transmitted signal is generated and above which a transmitted signal is generated.

Additionally, the electronics can contain monitoring logic such that a signal is not generated until a transmit state is reached. Although the transmit state can be activated simply whenever a pressure on/off type switch is activated or a pressure threshold signal intensity occurs, more sophisticated logic can be included so that the transmit state is not activated until a given pressure conditions persists for more than a set time or until a set pressure amplitude is achieved. Of course, the electronics include logic to determine when to stop the transmitted signal as well. Thus, the transmitted signal would stop or a stop signal would be generated when the on pressure state changes to the off pressure state, i.e., the activated on/off switches turn off or the continuous pressure sensor signal drops below the pressure threshold intensity.

Figure 1B:
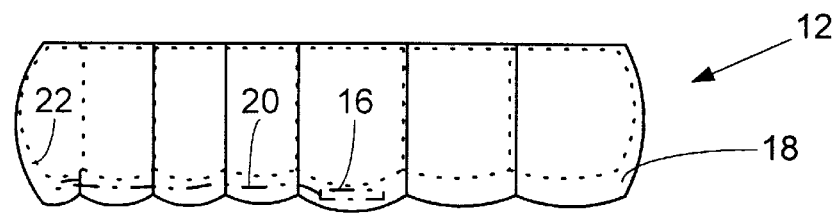
Figure 1C:
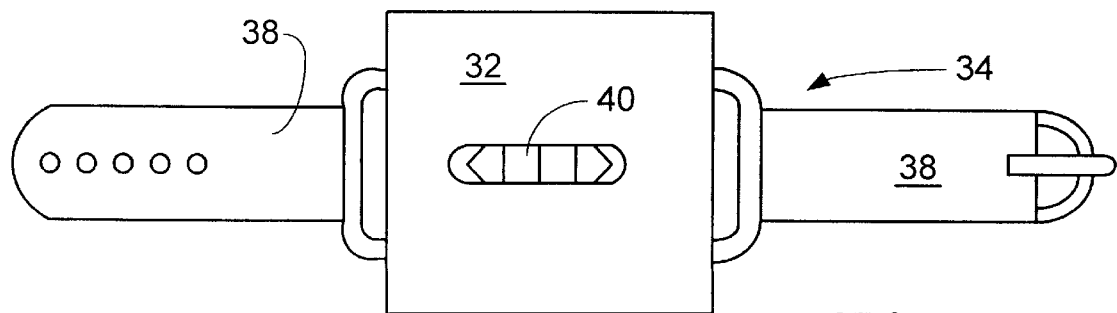

Referring now to FIG. 1a–c, a first embodiment of a mouth guard device of the present invention (shown to include a mouth guard and a writ alarm unit) can be seen to include a molded plastic mouth guard 12 as described in Section I above. This guard 12 is custom made to contours of a prospective wearer's teeth by molding a piece of plastic to a plaster mold of an upper teeth of the wearer. Pockets or sockets 14 are formed in the guard 12 to snugly fit around sides and biting surfaces of each individual tooth so the guard 12 will be comfortable and won't fall off the teeth. When inserted into the wearer's mouth, the guard 12 provides a protective layer of plastic between the upper and lower teeth.

Pressure activated elastomer switches 16 are embedded laterally in the molded plastic guard 12 flush with a biting surface of one or more teeth. These switches 16 are covered and hermetically sealed with a layer of flexible plastic 18. Also covered and sealed in the plastic 18 within the guard 12 are electrical wires 20 running from the switches 16 through a rear plastic wall 22 of the guard 12 into Section II 24, the molded plastic electronics compartment.

The compartment 24 includes a coin shape battery power source 26 and an optional holder (not shown) and a radio frequency transmitter 30. Section II or the plastic compartment 24 is molded to the plastic guard 12 (Section I) embedding the battery 26 and transmitter 30. When the wearer bites down on the guard 12, pressure is applied to the elastomer switches 16. This pressure causes the conductive particles contained in the elastomer switches 16 to conduct. This activates the transmitter 30 which sends a radio signal to activate an alarm 32 contained in a receiver unit 34. The compartment 24 also includes a radio antenna 36 associated with the transmitter 30 for proper signal projection.

Figure 2A:
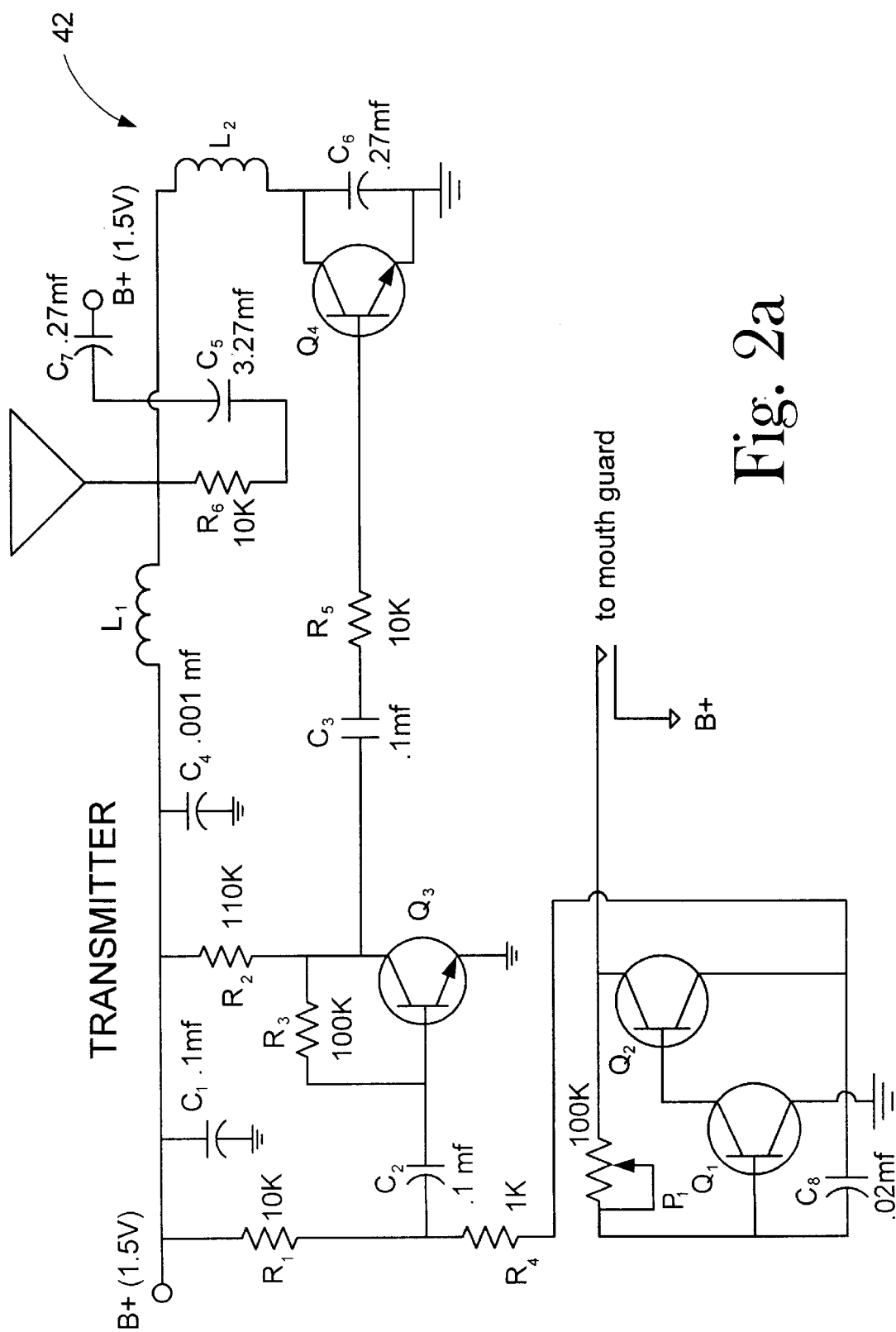
FIG. 2a is an electrical schematic of one embodiment of a transmitter.
Figure 2B:
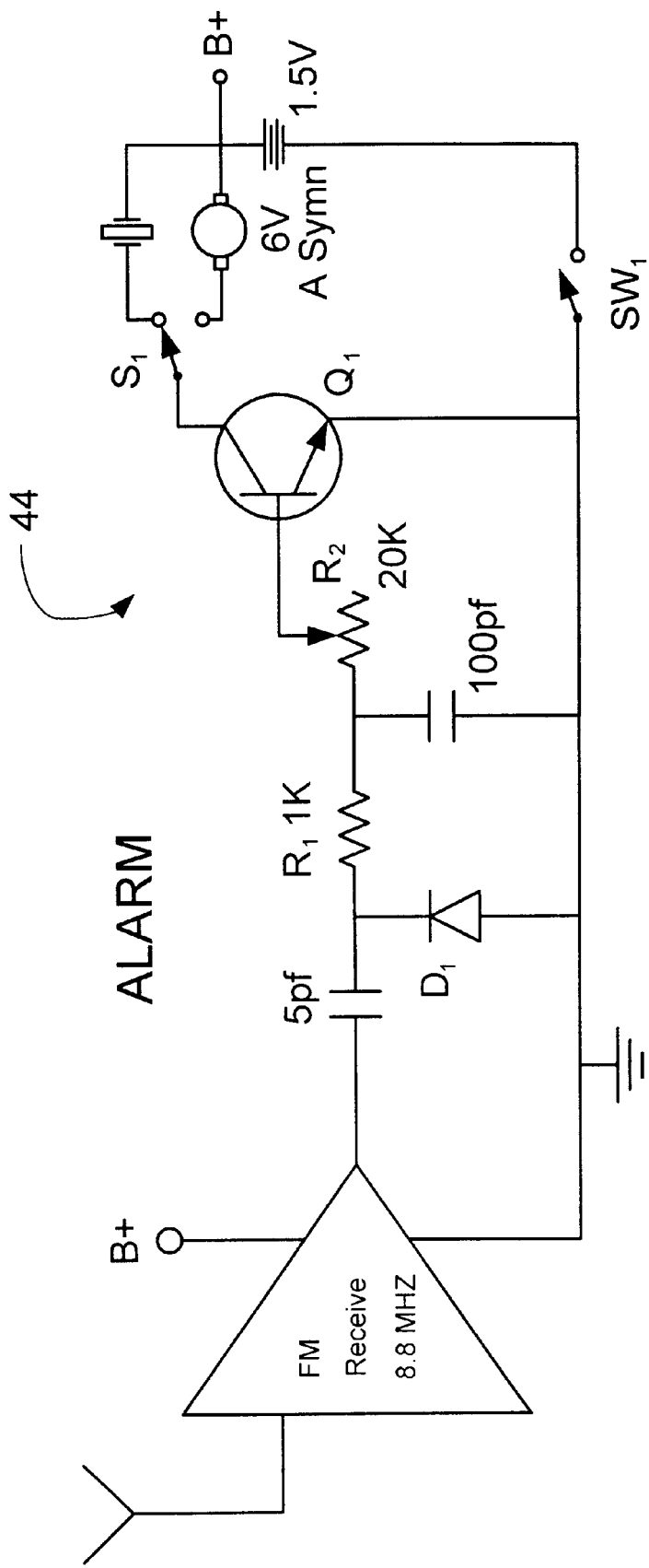
FIG. 2b is an electrical schematic of one embodiment of a receiver/alarm.

The combined device of FIGS. 1a–c also includes a receiving unit 34 which is shown in the figure as a wristband 38. The wristband 38 includes a power on/off switch 40 and the alarm 32. One embodiment of an electrical schematic of a monitoring and transmitting circuit generally 42 is shown in FIG. 2a; while FIG. 2b shows one embodiment of an electrical schematic for a receiver/alarm circuit generally 44.

Figure 3:
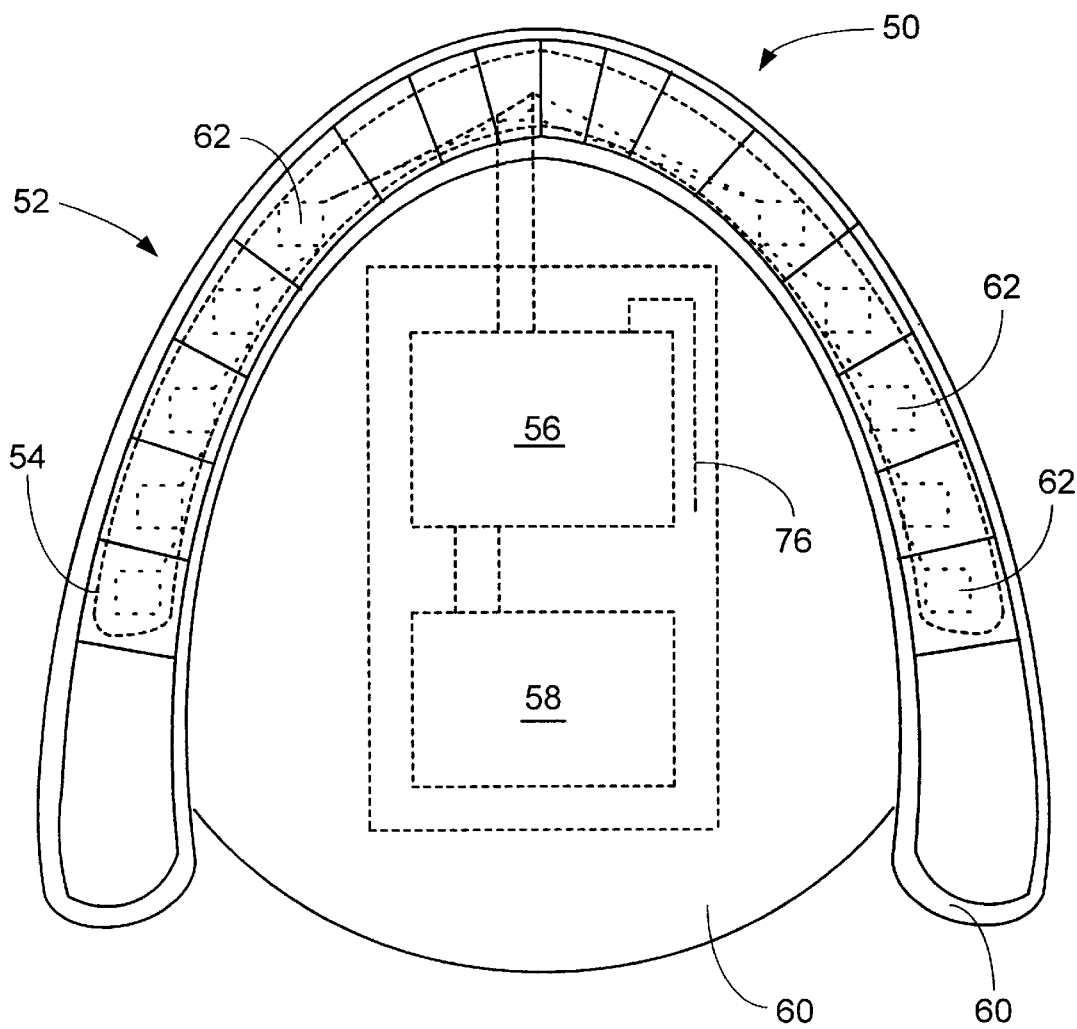
FIG. 3 is another embodiment of a mouth guard of the present invention.
Figure 4A:
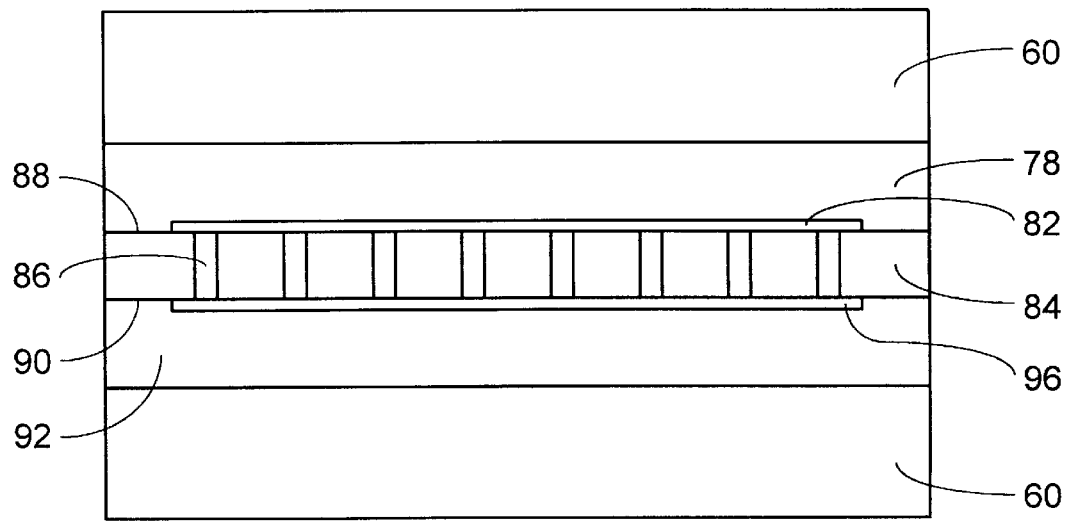
FIG. 4a is a cross-section view of a section of the membrane of FIG. 3 at line segment 1-1'.
Figure 4B:
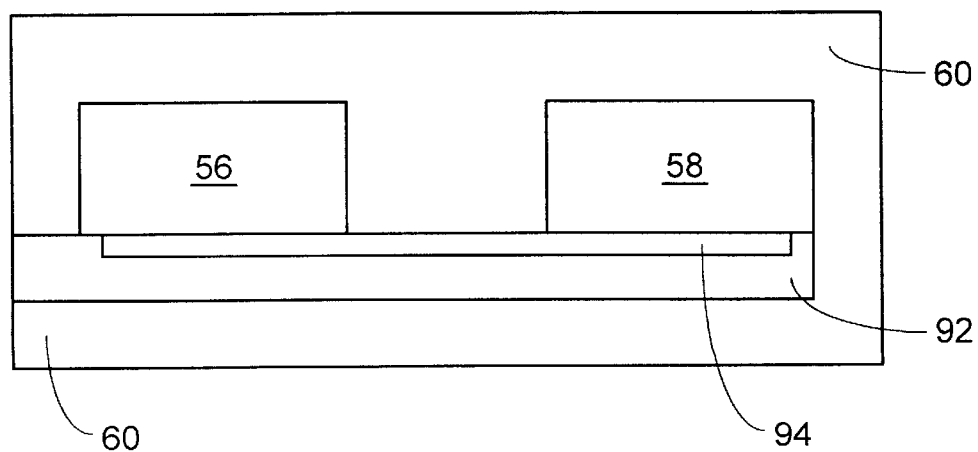
FIG. 4b is a cross-section view of a section of the chip and battery compartment of FIG. 3 at line segment 2-2'.

Referring now to FIG. 3, a second embodiment of a mouth guard of the present invention is shown generally 50, including a mouth piece 52 which fashioned to conform to a user's upper jaw and teeth. The mouth piece 52 includes a pressure sensitive membrane 54, a chip/transmitter 56 and a battery 58 for supplying power to the membrane 54 and the chip 56 which are in electric communication all encapsulated in a biocompatible plastic material 60 as shown in FIGS. 4a–b which are cross-sectional segment views. The preferred chip or microprocessor for use in this application is a PCM-170 chip available from RFM of Dallas, Tex. The preferred plastic material is a clear acrylic polymer such as so-called dental grade acrylic.

Figure 6:
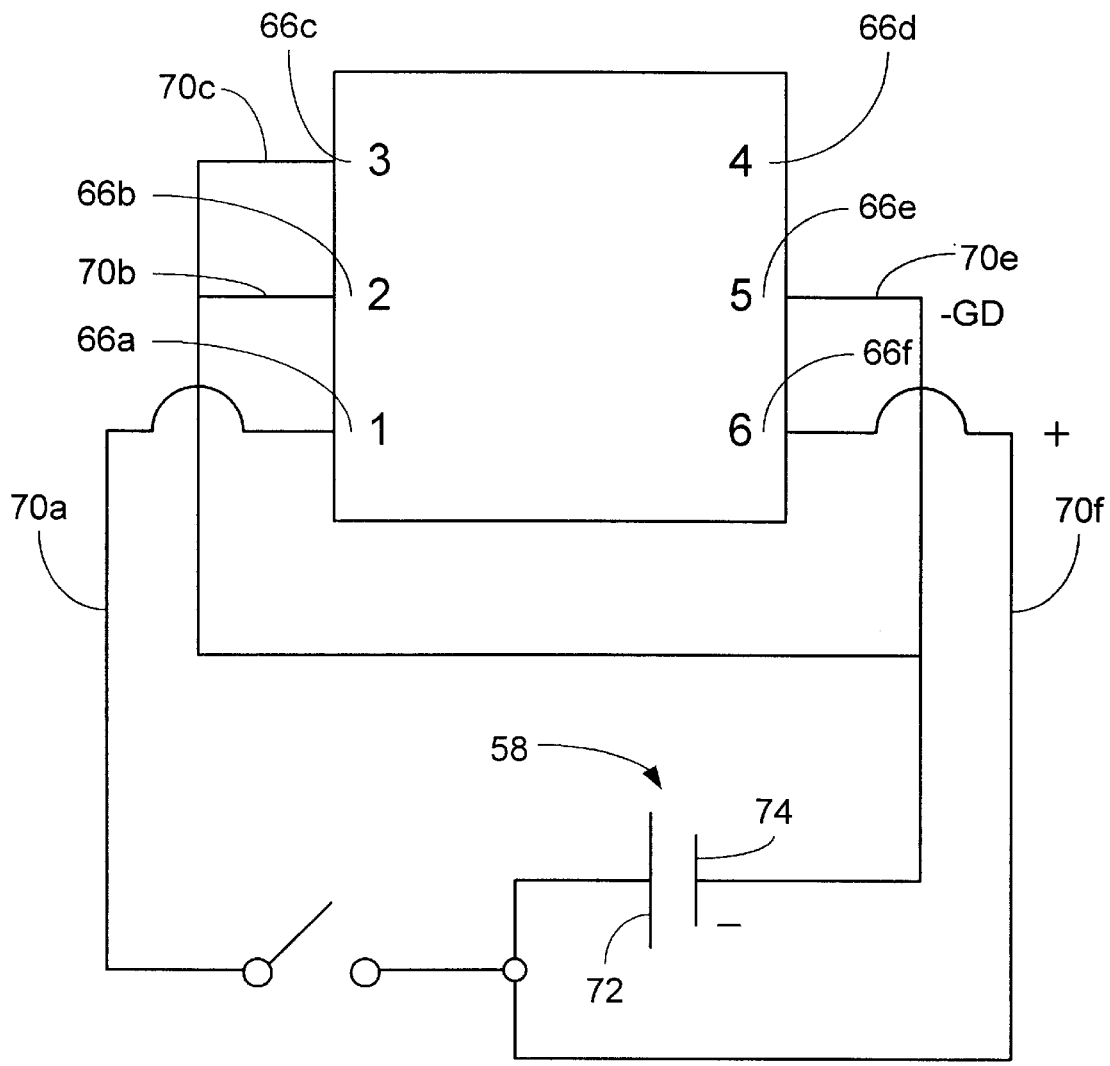
FIG. 6 is a schematic diagram of the pin arrangement of the chip associated with the mouth guard of FIG. 3.

The pressure membrane 54 includes a plurality of pressure switches 62. The switches 62 can all be in electrical communication with each other so that activation of any switch results is a change in state of the membrane as shown in FIGS. 5a–c or each switch can have its own individual circuit so that the device can determine which switch has been activated. As shown in FIG. 6, the chip or integrated circuit 56 includes a transmitter (not shown) and a plurality of pins 66a–f that are connected to a matching plurality of circuit elements ends 68a–f associated with circuit elements 70a–f of the membrane 54, as shown in FIGS. 5a–c and 6. (Note elements 70b and 70c do not exist in the embodiment and would be used on chip based data acquisition, data analysis and processing and storage).

The pressure switches 62 are on/off type switches that are normally in an open or "off" state changing to a closed or "on" state when sufficient pressure is applied across the membrane 54 so that at least one switch 62 changes to its closed or "on" state causing the entire membrane 54 to be in its closed or "on" state. Obviously, if each switch has its own circuit, then the microprocessor/transmitter 56 will be able to determine which switches have been activated, data that could be used to analysis pressure patterns during bruxing episodes. The pin 66a is connected to element 70a at element end 68a which corresponds to one side of the membrane switch circuit. The pin 66f is connected to element 70f at element end 68f which corresponds to the other side of the membrane switch circuit and is also connected to a positive terminal 72 of the battery 58. The pins 66b,c and e are connected to ground or a negative terminal 74 of the battery 58. The pin 66d is associated with an antenna 76 for the transmitter 56.

Thus, when the membrane switch closes due to pressure exerted on the membrane during a grinding episode, power flows to the transmitter 56 which generates a signal indicating a change of state of the pressure membrane 54 or an individual switch 62. Of course, the pressure switches 62 can also be load cells or elastomer membranes instead of simple on/off switches contained in the pressure membrane 54. If load cells, elastomer membranes, strain gauges or other pressure sensors are used, the device 50 can be used not only to measure the frequency and duration of grinding episodes (signal on, signal off and the period of time between signal on and signal off), but also the amplitude and/or direction of the pressure experienced by the sensors during each grinding episode.

Looking now in more detail at FIGS. 3 and 5a–c, the membrane 54 is a composite structure including a first copper clad sheet 78 having a first circuitry 80 associated therewith, which circuitry 80 includes a plurality of electrically connected wire mesh regions 82. The membrane 54 also includes a middle, insulator sheet 84 having perforations 86 therethrough and adhesive layers (not shown) associated with its top surface 88 and bottom surface 90. The membrane 54 also includes a second copper clad sheet 92 having a second circuitry 94 associated therewith, which second circuitry 94 includes a plurality of electrically connected wire mesh regions 96 corresponding to the regions 82 of the first copper circuit layout 80. The sheets 78, 84 and 92 are preferably composed of a polyamide such as nylon and particularly of a polycaprolactam polymer made by DuPont sold under the trade name PYRALUX®. Of course, any polymeric material can be used provided it can be sealed into a usable membrane pressure sensitive device.

Although the perforations 86 can be associated with the entire middle sheet 84, the perforations 86 are preferentially located in patterned arrays 98 corresponding to the meshes 82 and 96. The meshes 82 and 96 are preferentially composed of thin copper lines 100 inscribed, printed or etched (or by another suitable technique) diagonally within a containing square or rectangular perimeter 102. The diagonal lines 100 associated with meshes 82 and 96 can be physically manifested in the same direction, but are preferentially, and as shown in the figures, physically manifested diagonally opposed so that the resulting pattern of the composite membrane is a grid pattern and preferably a perpendicular or square grind pattern.

The copper lines with the perforations interposed therebetween form the basis for the pressure switches of the pressure sensitive membrane of the present invention. Thus, when pressure is applied to the membrane in a mesh region, the pressure brings the copper lines into electrical contact through one or more perforations closing the switch circuit or membrane circuit. Once the circuit is closed, the integrated circuit, microprocessor or chip senses the change in state and activates the transmitter which transmits a signal while the circuit is closed. When pressure ceases, the circuit re-opens which is sensed by the chip and the transmitter is deactivated and the signal stops.

Figure 7:
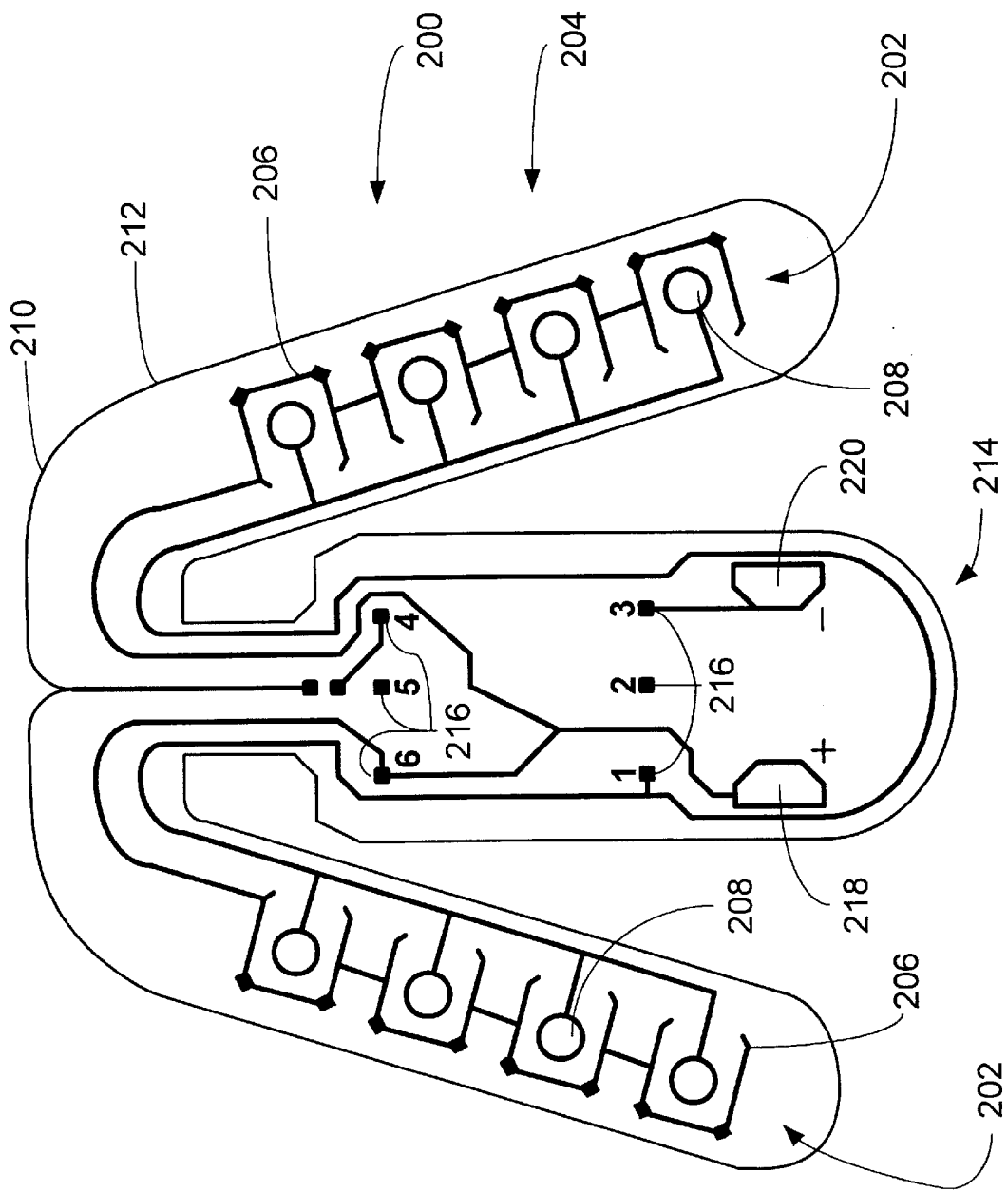
FIG. 7 is another embodiment of a mouth guard circuitry board designed to accommodate a plurality of tactile metal dome switches.

Referring now to FIG. 7, another embodiment of a mouth guard circuitry board generally 200 of this invention is shown which is designed to accommodate a plurality of in tactile metal dome switches 202. The dome switches can all have the same pressure rating (the amount of pressure that must be applied to the switch to cause the dome to defect down and close the circuit) or each switch can have a different rating or any other combination of ratings. The circuit board 200 is in the general shape of a wearer's teeth outline 204 and includes a plurality of interconnected switch positive circuit elements 206 and interconnected negative circuit elements 208. The circuit board 200 also includes an antenna 210 which follows an outer contour 212 of the board 200 and a pallet region 214 having six sites 216 which are designed to come into electric contact pins of a six pin IC and a positive battery terminal node 218 and negative battery terminal node 220. Each pair of positive and negative circuit elements is designed to receive a single dome switch. Thus, the board 200 of FIG. 7 is designed to accommodate 8 dome switches. When pressure is applied across a given dome switch mounted on a give pair of elements, then the metal dome of the switch will close the open circuit across the given pair of elements activating the IC and causing a signal to be sent to a receiver for processing. Of course, this board is designed to be encased in a polymeric cover to electrically isolate the board and board components from the fluids in the wearer's mouth.

The next three figures relate to a second type of membrane switch than the membrane switch described previously. The membrane switches broadly include a top layer, a bottom layer and a middle layer interposed therebetween. The top layer can be either one element of the open switch circuit or a shunt element. The middle layer is a sheet having a specified density of perforation therethrough, where the perforations have a size (diameter) and a preferably arrayed in a column-row arrangement. The bottom layer includes the majority of the circuit elements for connecting a battery and an IC to the circuit elements so that when a given pressure is exerted across the membrane, the membrane is changed from an open-circuit to a closed circuit which activates the IC causing the antenna to transmit a signal.

Figure 8A:
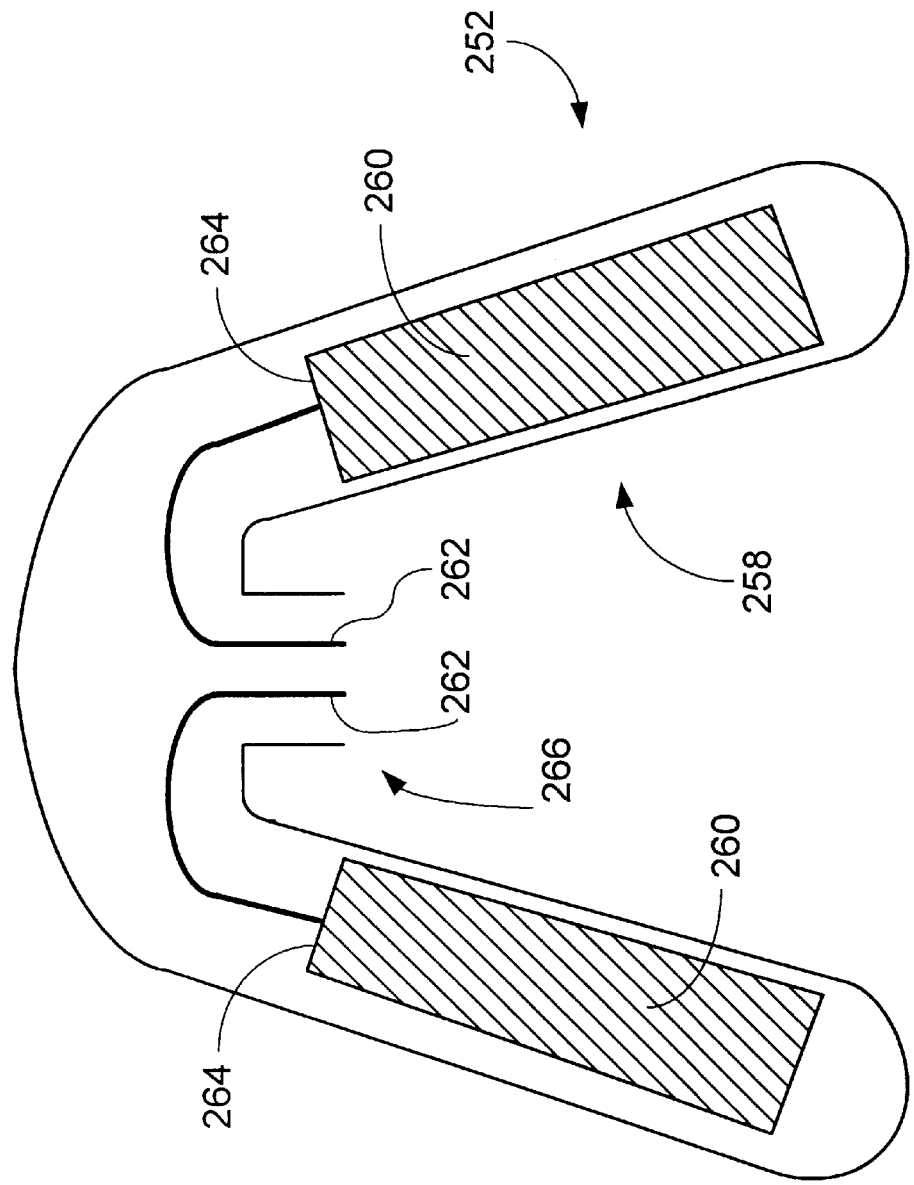
FIGS. 8a–c is a first embodiment of a second type of membrane switch of this invention.
Figure 8B:
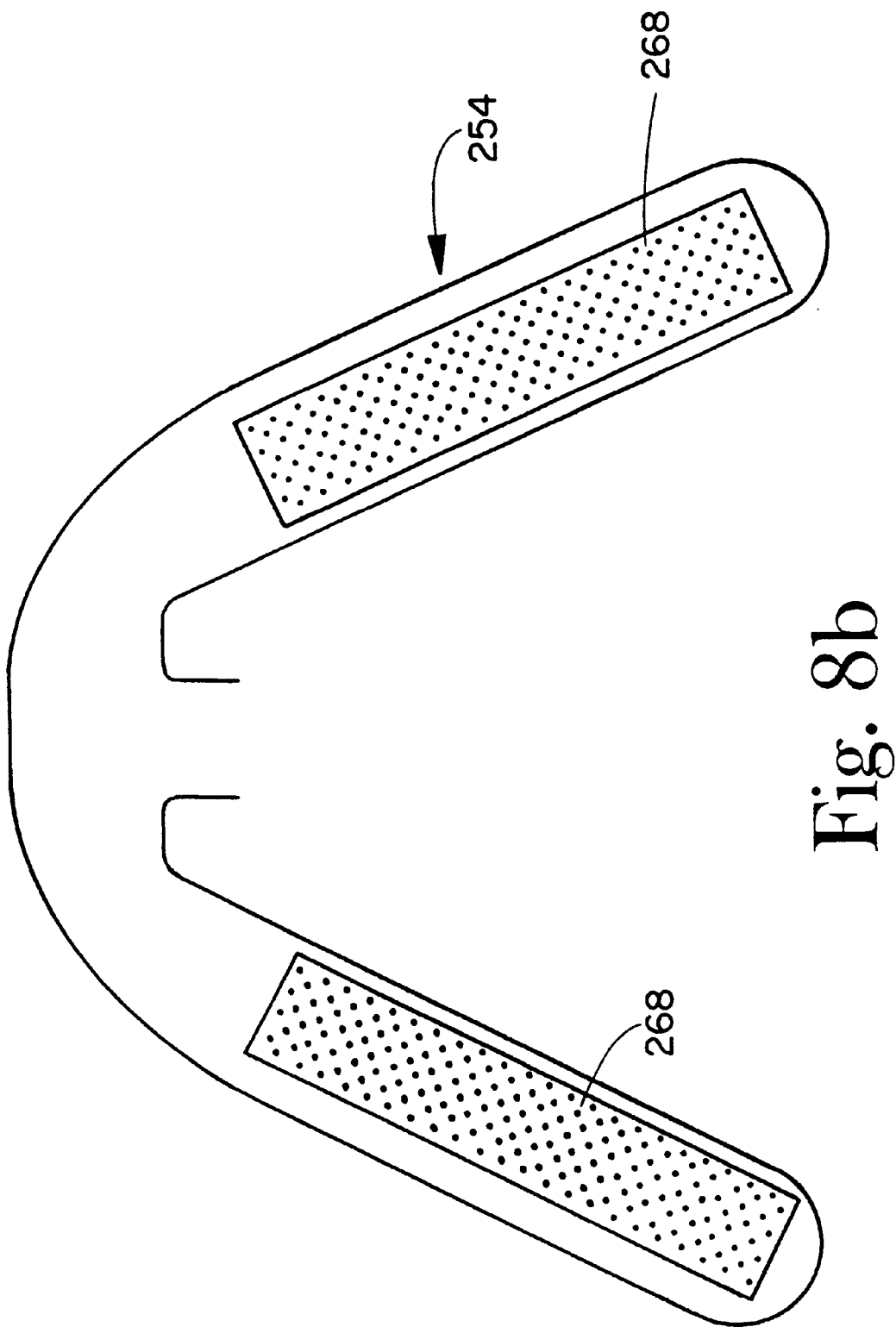
Figure 8C:
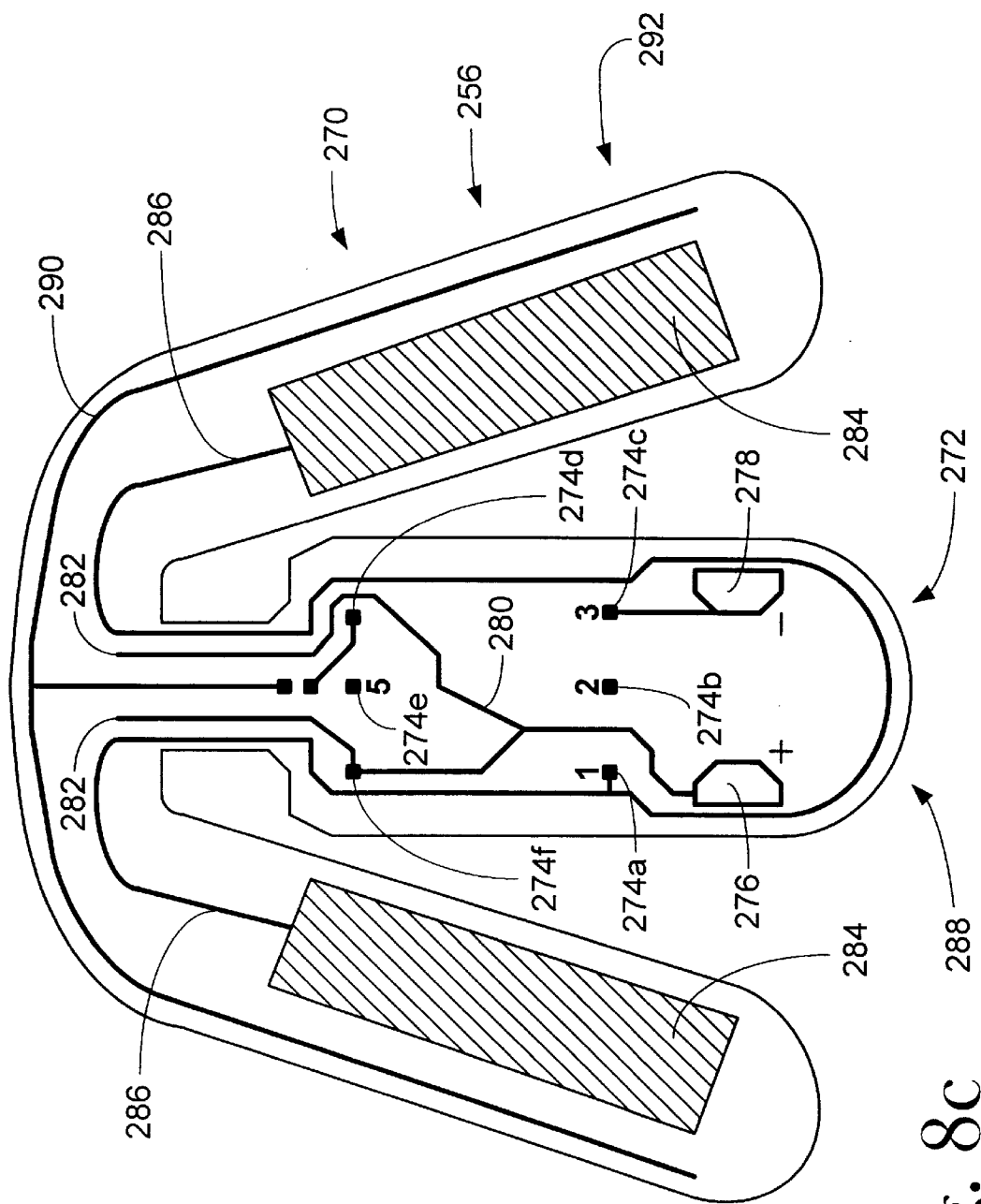

Referring now to FIGS. 8a–c, a first embodiment of a second type of membrane switch generally 250 of this invention is shown. The membrane switch 250 includes a top layer 252, a middle layer 254 and a bottom layer 256. The top layer 252 is in the general shape of a wearer's teeth outline 258 and includes two rectangular shaped, positive circuit elements 260, each element 260 having a wire 262 extending from its forward end 264 and terminating at a pallet position 266. The middle layer 256 has substantially the same general shape as the top layer and is designed to be overlaid by the top layer 252. The middle layer 254 includes two rectangular shaped, perforated members 268 positioned to correspond to the positive circuit elements 260 after overlay. The bottom layer 258 has a tooth region 270 and a pallet region 272. The pallet region 272 includes six IC nodes 274a–f numbered 1–6 and a positive battery terminal node 276 and a negative battery terminal node 278. The pallet region 272 also includes a positive wire element 280 extending from the positive battery node 276 and terminating in two ends 282 one end connected to IC node 6, 274f. The tooth region 270 includes two rectangular shaped, negative circuit elements 284 and a wire 286 interconnecting the elements 284 and connecting the elements to IC node 1, 274a and following an outer contour 288 of the pallet region 272. The bottom layer 258 also includes an antenna 290 extends from the pallet region 272 and follows a forward outer contour 292 of the tooth region 270. When pressure is applied across the membrane sufficient to bring one or both of the positive elements in contact with the negative elements, then the switch will close activating the IC and causing a signal to be sent to a receiver for processing. Of course, this board is designed to be encased in a polymeric cover to electrically isolate the board and board components from the fluids in the wearer's mouth. The perforated sheets useful in the second-type of membrane switches of the present invention are available from C&K Components, Inc. of Watertown, Mass. These perforated sheets used as the middle layer can be produced or manufactured with different threshold pressure rating by controlling both the number and diameter of the perforations in the sheet. Thus, activation pressures between about 5 and 20 psi can be constructed with dot diameters between about 0.1 mm and about 1 mm and dot pitches (number of dots per cm$^2$) between about 0.1 mm and about 5.0 mm distance between dots on a regular grid, i.e., 5.0 represents the least dots per cm$^2$ and 0.1 represents the most dots per cm$^2$. The preferred sheets have pressure activations between about 8 and about 15 psi based on a preferred pitch between about 2.0 and about 0.5 and a dot diameter between about 0.2 mm and about 0.5 mm.

Figure 9C:
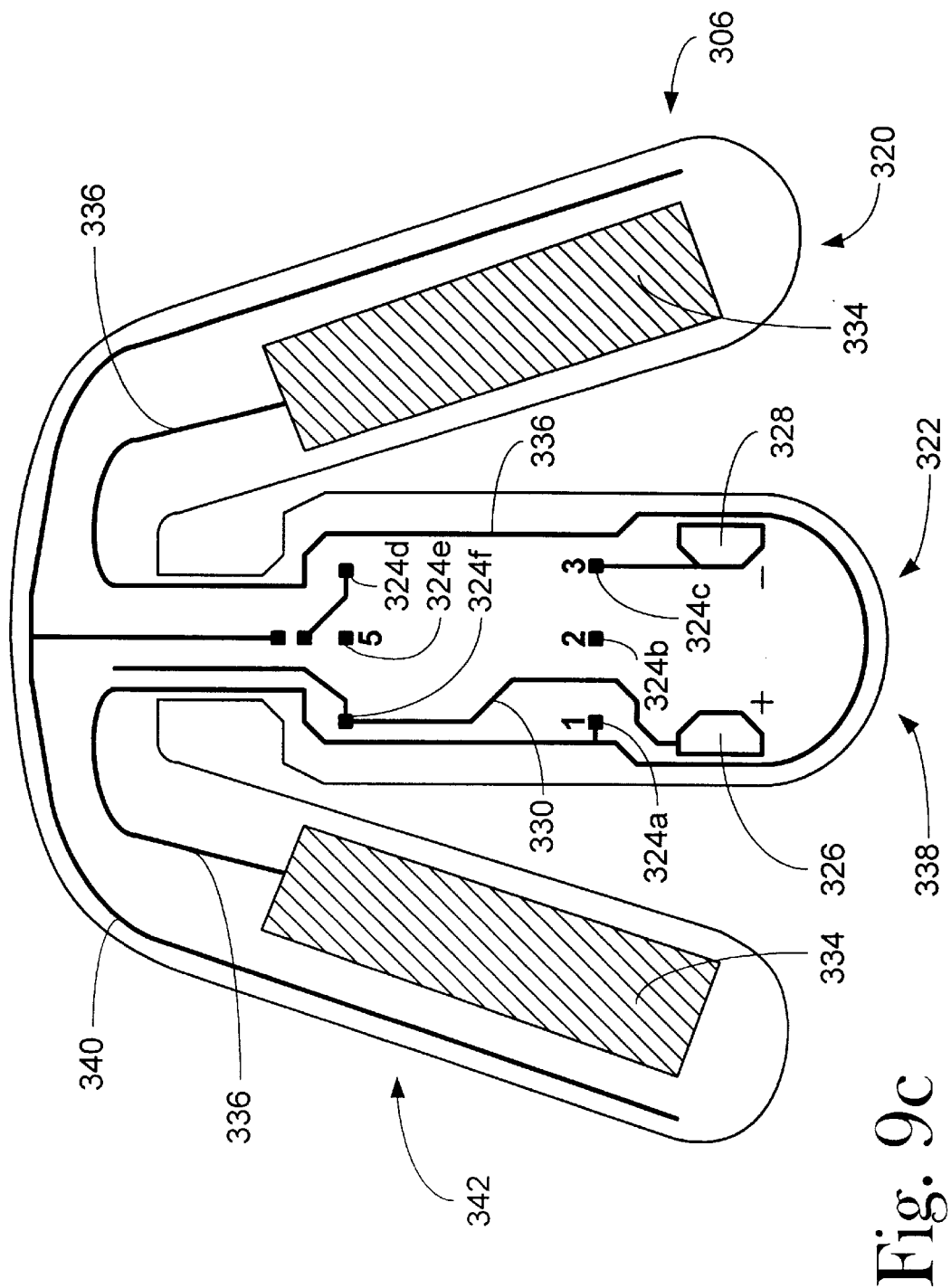

Referring now to FIGS. 9a–c, a second embodiment of a second type of membrane switch generally 300 of this invention is shown. The membrane switch 300 includes a top layer 302, a middle layer 304 and a bottom layer 306. The top layer 302 is in the general shape of a wearer's teeth outline 308 and includes two rectangular shaped, positive circuit elements 310, each element 310 having a wire 312 extending from its forward end 314 and terminating at a pallet position 316. The middle layer 304 has substantially the same general shape as the top layer and is designed to be overlaid by the top layer 302. The middle layer 304 includes two rectangular shaped, perforated members 318 positioned to correspond to the positive circuit elements 310 after overlay. The bottom layer 306 has a tooth region 320 and a pallet region 322. The pallet region 322 includes six IC nodes 324a–f numbered 1–6 and a positive battery terminal node 326 and a negative battery terminal node 328. The pallet region 322 also includes a positive wire element 330 extending from the positive battery node 326 and electrically connected to IC node 6, 324f and terminating in an end 332. The tooth region 320 includes two rectangular shaped, negative circuit elements 334 and a wire 336 interconnecting the negative elements 334 and connecting the elements to IC node 1, 324a and following an outer contour 338 of the pallet region 322. The bottom layer 308 also includes an antenna 340 extends from the pallet region 322 and follows a forward outer contour 342 of the tooth region 320. When pressure is applied across the membrane sufficient to bring one or both of the positive elements in contact with the negative elements, then the switch will close activating the IC and causing a signal to be sent to a receiver for processing. Of course, this board is designed to be encased in a polymeric cover to electrically isolate the board and board components from the fluids in the wearer's mouth.

Figure 10B:
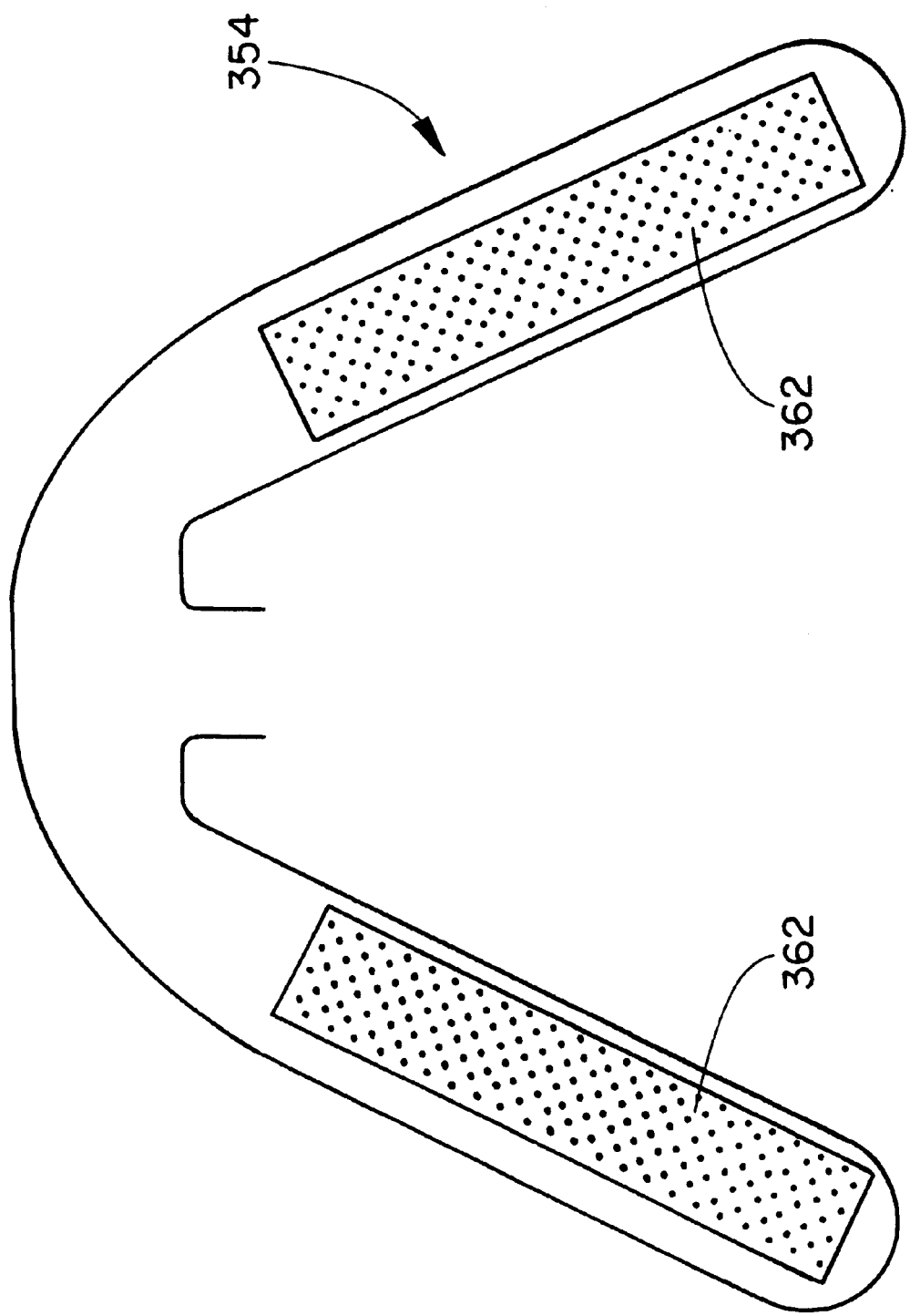
Figure 10C:
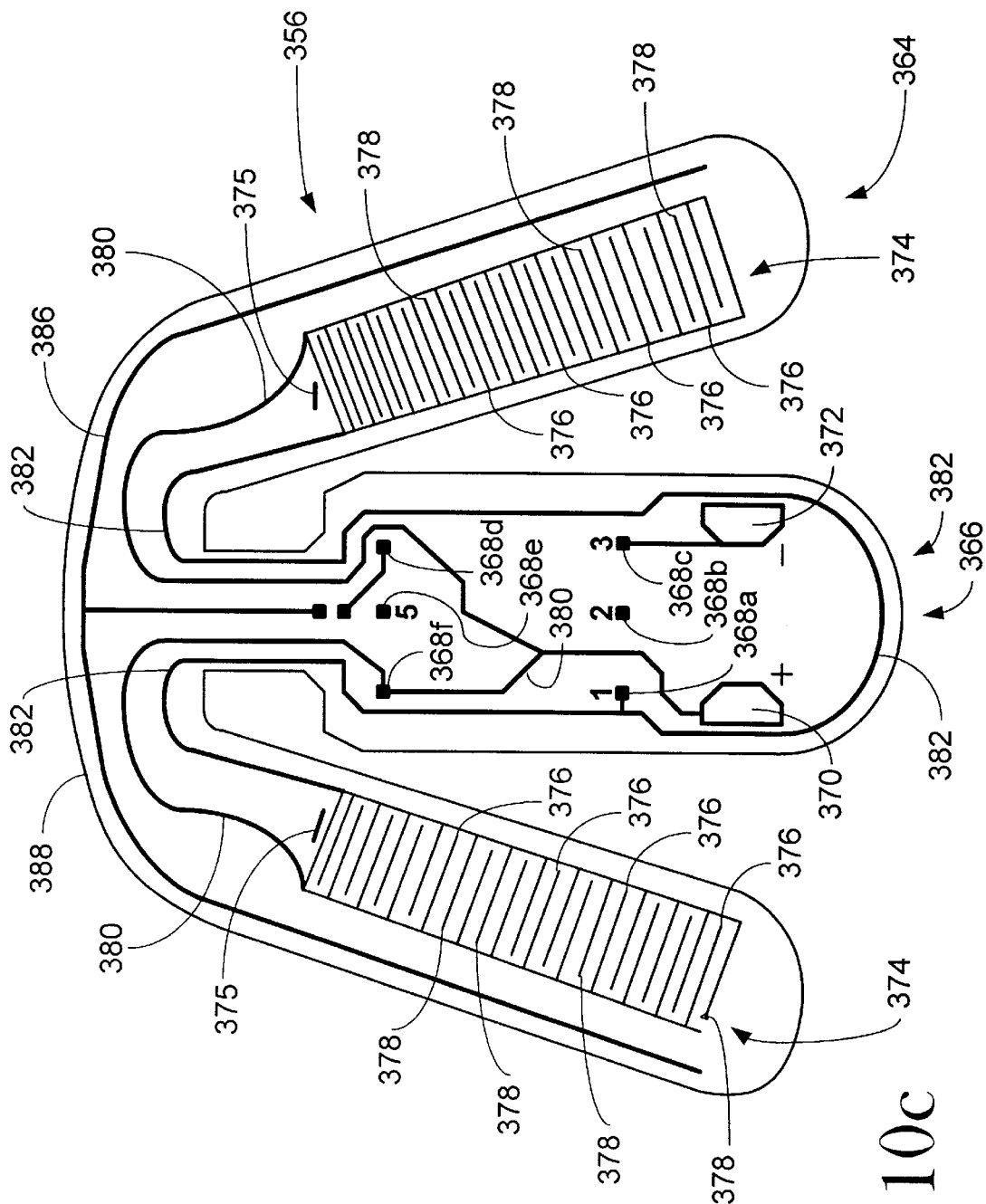

Referring now to FIGS. 10a–c, a third embodiment of a second type of membrane switch generally 350 of this invention is shown. The membrane switch 350 includes a top layer 352, a middle layer 354 and a bottom layer 356. The top layer 352 is in the general shape of a wearer's teeth outline 358 and includes two rectangular shaped, shunt elements 360. The middle layer 354 has substantially the same general shape as the top layer and is designed to be overlaid by the top layer 352. The middle layer 354 includes two rectangular shaped, perforated members 362 positioned to correspond to the shunts 360 after overlay. The bottom layer 356 has a tooth region 364 and a pallet region 366. The pallet region 366 includes six IC nodes 368a–f numbered 1–6 and a positive battery terminal node 370 and a negative battery terminal node 372. The tooth region 364 includes two rectangular shaped areas 374 comprising an interpenetrating network 375 of positive wires 376 and negative wires 378. The positive wires 376 are connected to a positive lead wire 380 which makes electrical contact with IC node 6, 368f and the positive battery terminal node 370. The negative wires 378 are connected to a negative lead wire 382 which makes electrical contact with IC node 1, 368a and follows an outer contour 384 of the pallet region 366. The bottom layer 356 also includes an antenna 386 extends from the pallet region 366 following a forward outer contour 388 of the tooth region 370. When pressure is applied across the membrane sufficient to bring the shunt element in contact with a positive and negative wire of the interpenetrating wire networks, then the switch will close activating the IC and causing a signal to be sent to a receiver for processing. Of course, this board is designed to be encased in a polymeric cover to electrically isolate the board and board components from the fluids in the wearer's mouth.

Of course, in any of the embodiments of the second-type of membrane switch, the positive and negative elements can be reversed without affecting the operation of the guard. Additionally, the circuit elements and IC used can be any circuit elements or IC that allow the pressure switch to activate the control circuitry in the IC causing the IC to transmit a signal from the antenna to a receiver which will then receive and act on the signal.

Morever, the battery included in each of the guard embodiments of the present invention can be replaced by a thickened antenna which acts as the negative terminal of the battery and is designed to extract electric energy from a field bathing the guard when the open circuit of a pressure switch in the mouth is closed. The field will then cause a current to flow through the device activating the IC and causing the IC to transmit a signal which is received and acted upon by the receiver.

Figure 11:
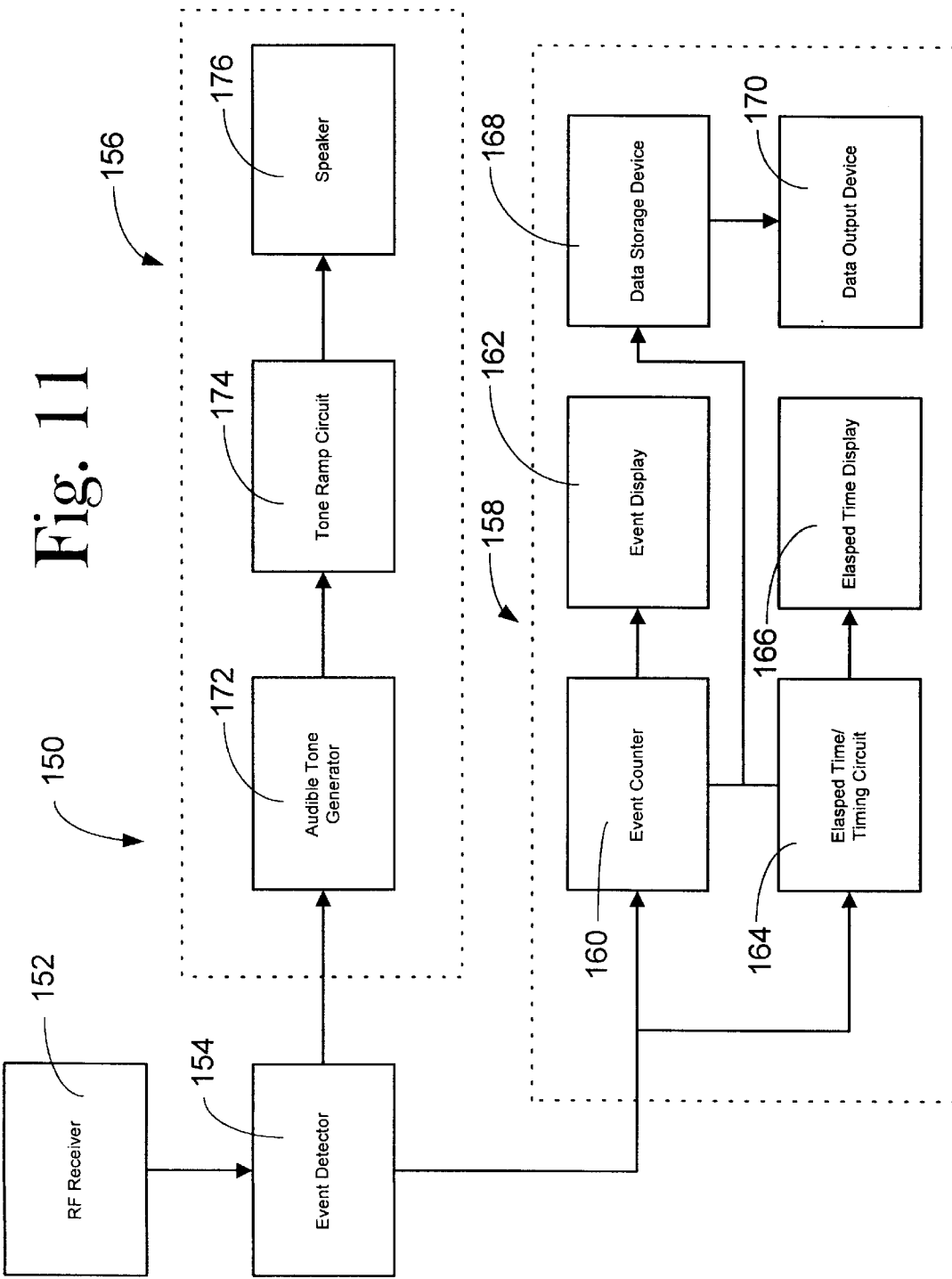
FIG. 11 is a schematic block diagram of another embodiment of the receiver unit of this invention.

Referring now to FIG. 11, the receiver/data acquisition/bio-feed back unit 150 of this invention broadly includes the following component: an RF receiver 152, an event detector 154, a bio-feed back unit 156 capable of generating an human cognizable response, and optionally a data acquisition system 158. The data acquisition system 158 can include an event counter 160, an event display 162, an elapsed time/timing circuit 164, an elapsed time display 166, a data storage device 168 and a data output unit 170. The bio-feed back unit 156 can include an audible tone generator 172, a tone ramp circuit 174 and a speaker 176. Of course, any other type of bio-feed back unit can be used such as a vibrator or other pressure inducing unit. The bio-feed back unit could also be an ear piece having a receiver, an event detector, a tone generator, a tone ramp circuit and a speaker. It should be understood that the bio-feed back unit can be any unit capable of generating an human cognizable response, conscious or subliminal.

EXAMPLES

The following examples are include for the sake of completeness of disclosure and to illustrate the methods of making the compositions and composites of the present invention as well as to present certain characteristics of the compositions, but in no way are these examples included for the sake of limiting the scope or teaching of this disclosure.

Example 1

This example illustrates the construction of a receiver/data acquisition/bio-feed back unit to be used in conjunction with the mouth guards of the present invention. Although this constructed unit is capable of receiving the transmitted signal from the mouth piece and in response store the data for later analysis and generating an human cognizable response, this unit is by no means intended to be limiting and it should be recognized that any receiver, data acquisition and bio-feed back apparatus can be used as well.

Figure 12:
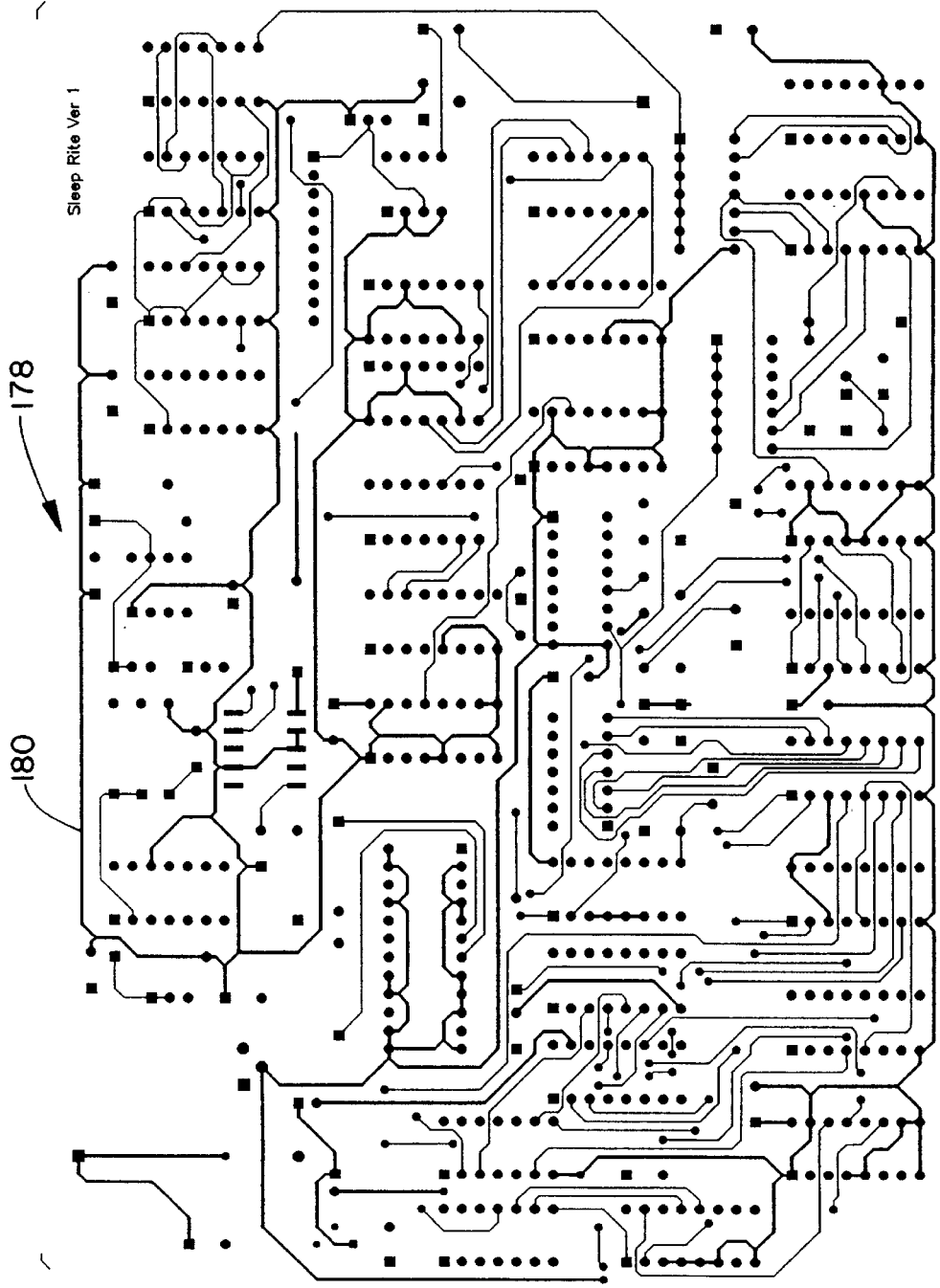
FIG. 12 is a top view of a top of one preferred printed circuit board for the receiver unit of FIG. 11.
Figure 13:
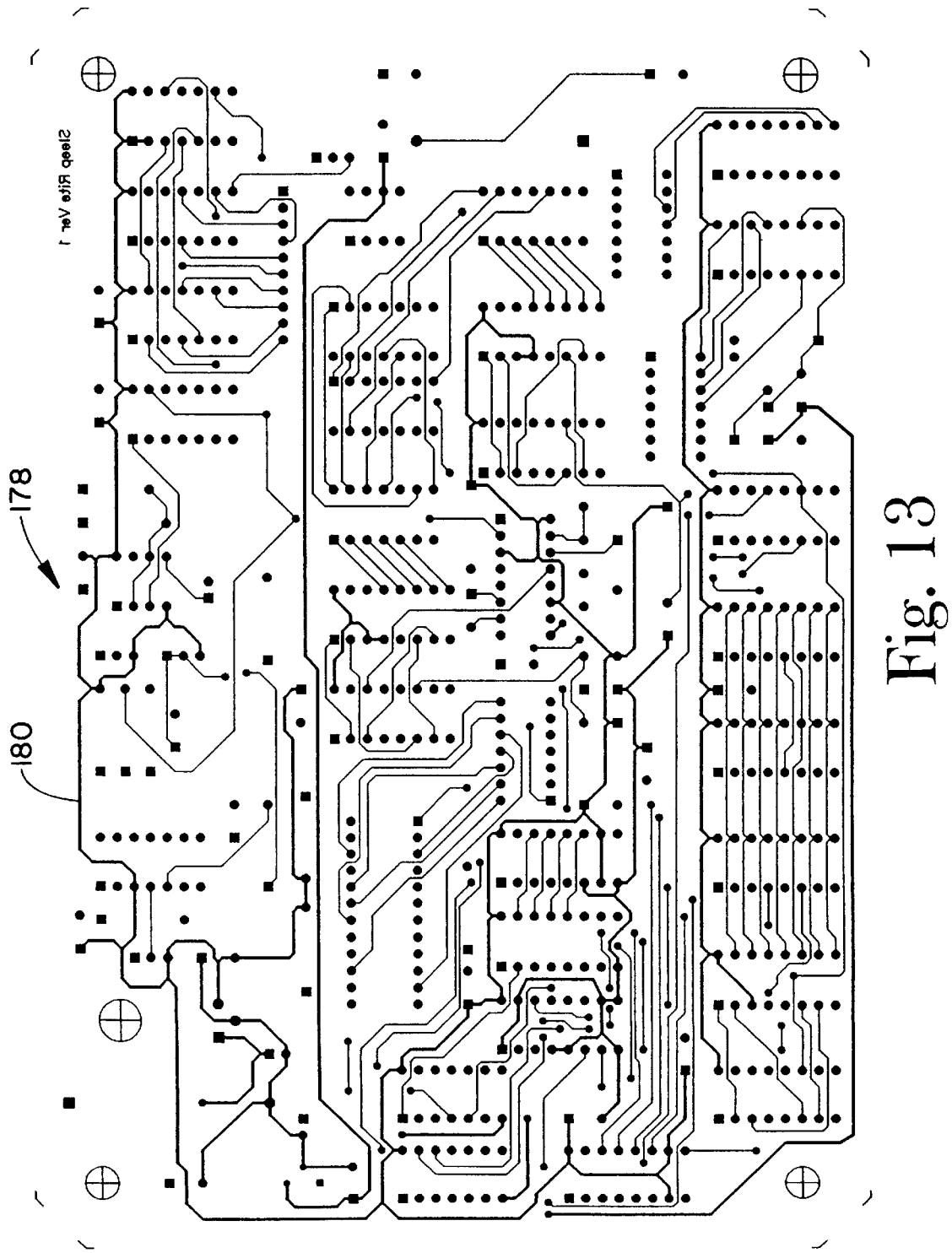
FIG. 13 is a top view of a bottom of printed circuit board of FIG. 12.
Figure 14:
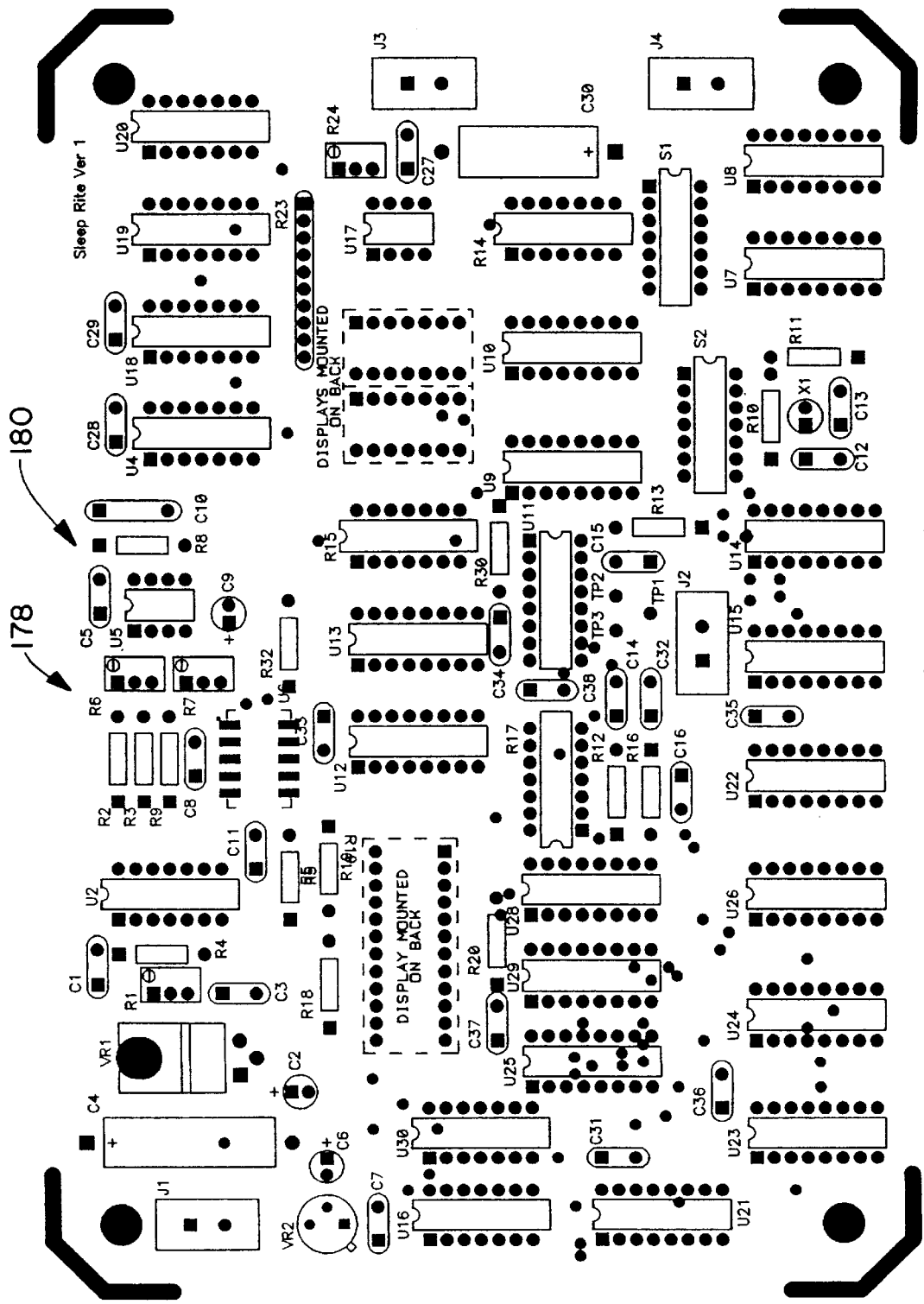
FIG. 14 is a component schematic diagram for the placement of components on the printed circuit board of FIG. 11.
Figure 15:
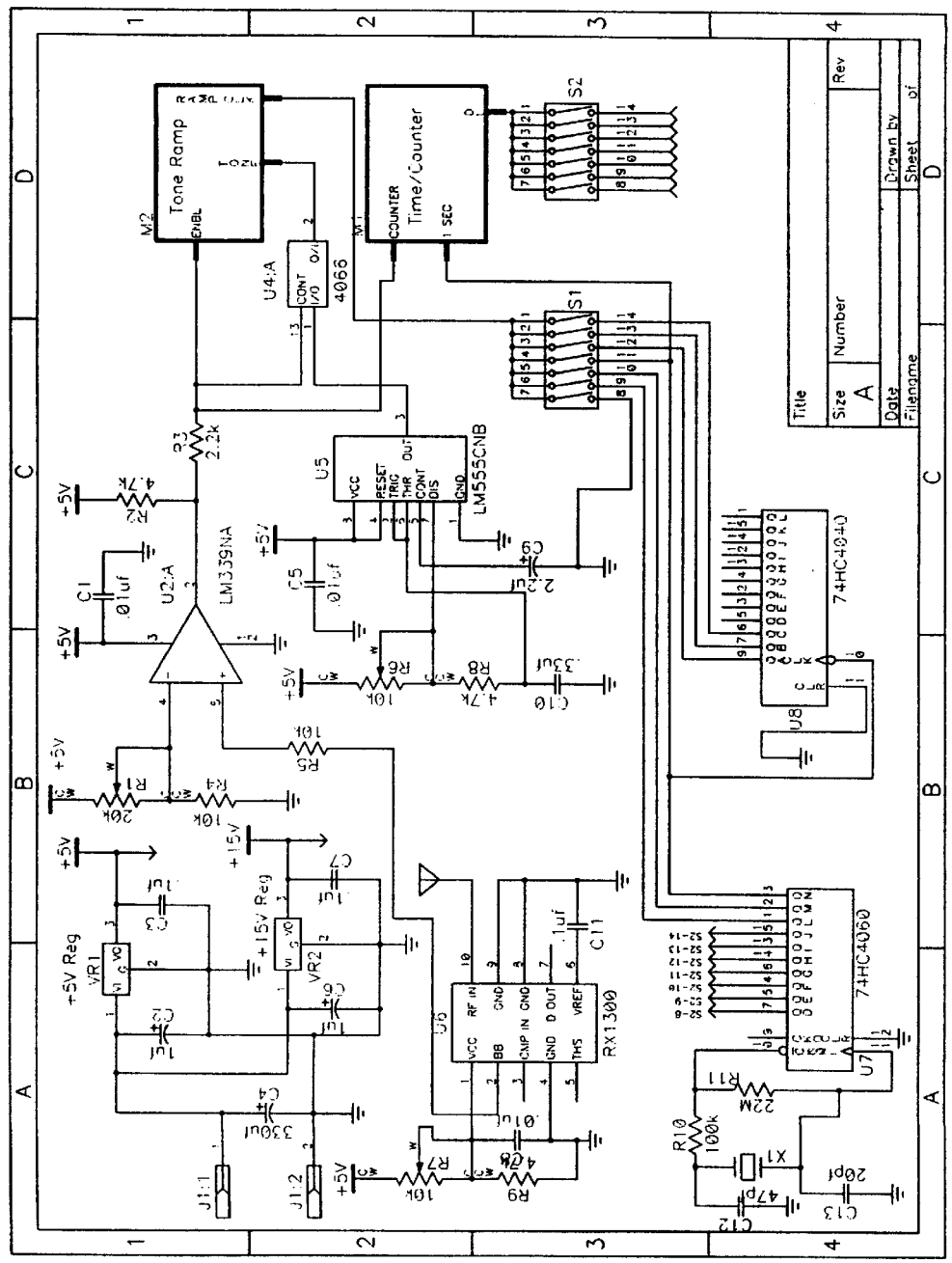
FIG. 15 is an electrical schematic diagram of the receiver of FIG. 11.
Figure 16:
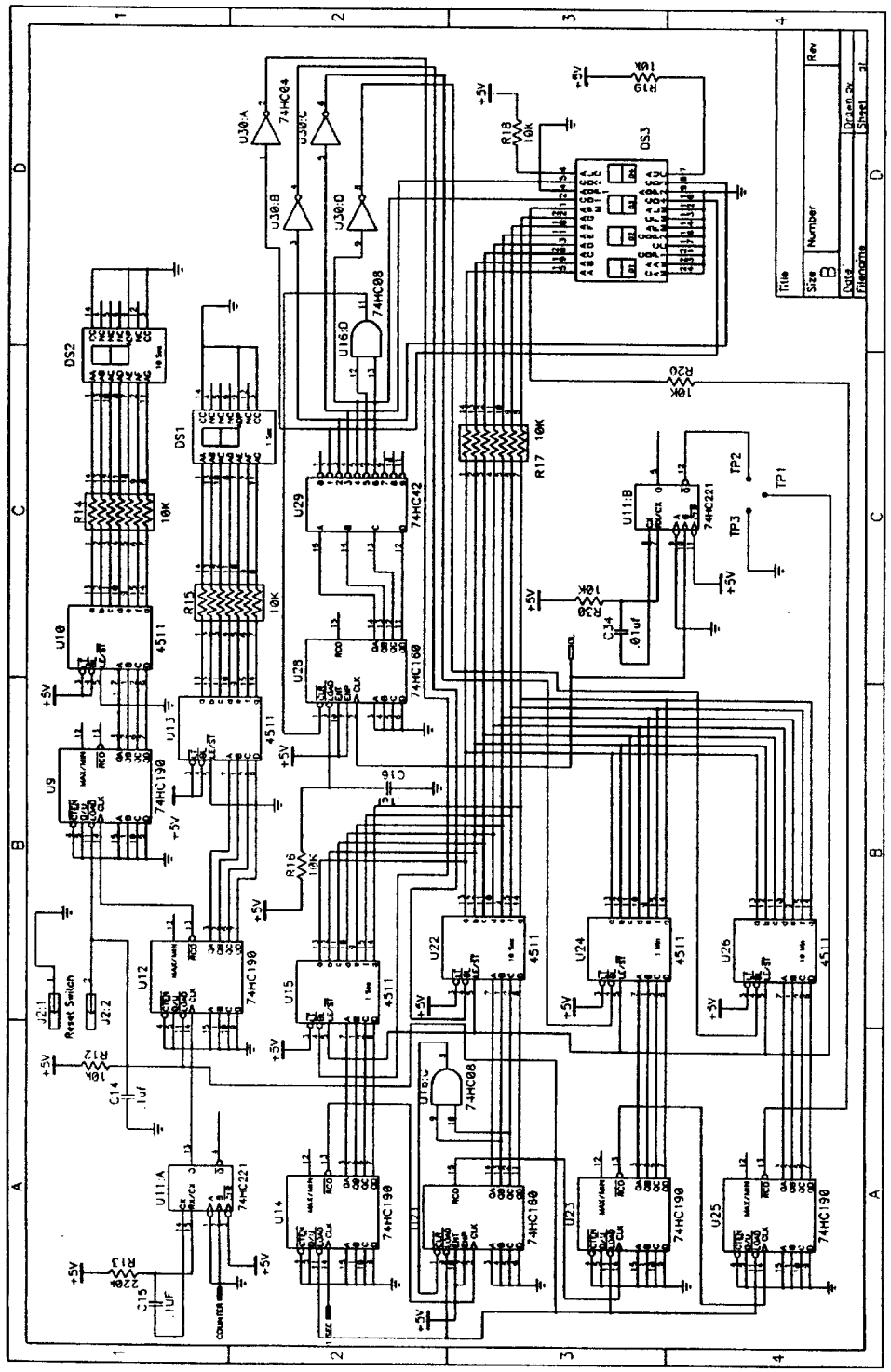
FIG. 16 is an electrical schematic diagram of the time/counter of FIG. 12.
Figure 17:
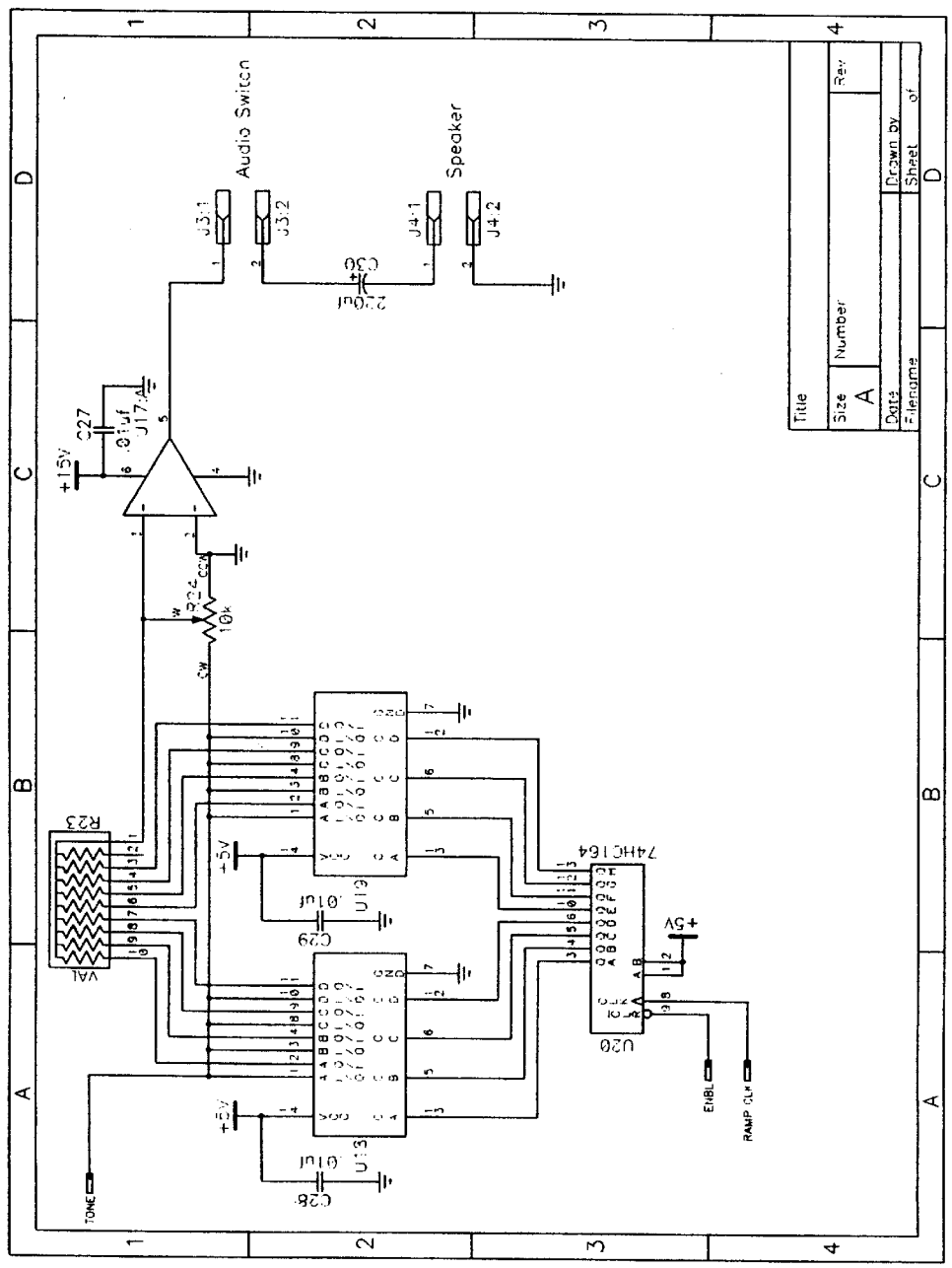
FIG. 17 is an electrical schematic diagram of the tone ramp of FIG. 12.

The unit 150 can include composed of a printed circuit board 178 having a circuit layout 180 as shown in FIGS. 12, 13, and 14 where the circuit layout is designed to implement schematic diagrams shown in FIGS. 15–13.

The board 178 includes the following list of components and corresponding reference numbers for proper placement of the components on the printed board 178 according to the layout 180 shown in FIG. 10:

| Component/Element # | Ref. No. | Component/Element # | Ref. No. |
|---|---|---|---|
| capacitor 0.01µF | C1 | capacitor 1µF | C2 |
| capacitor 0.1µF | C3 | capacitor 330µF | C4 |
| capacitor 0.01µF | C5 | capacitor 1µF | C6 |
| capacitor 0.1µF | C7 | capacitor 0.01µF | C8 |
| capacitor 2.2µF | C9 | capacitor 0.33µF | C10 |
| capacitor 0.1µF | C11 | capacitor 47pF | C12 |
| capacitor 20µF | C13 | capacitor 0.1µF | C14 |
| capacitor 0.1µF | C15 | capacitor 0.1µF | C16 |
| capacitor 0.01µF | C27 | capacitor 0.01µF | C28 |
| capacitor 0.01µF | C29 | capacitor 220µF | C30 |
| capacitor 0.1µF | C31 | capacitor 0.1µF | C32 |
| capacitor 0.1µF | C33 | capacitor 0.01µF | C34 |
| capacitor 0.01µF | C35 | capacitor 0.01µF | C36 |
| capacitor 0.01µF | C37 | capacitor 0.1µF | C38 |
| LED display | DS1 | LED display | DS1 |
| LED display | DS2 | connector 10F | J1 |
| connector 10F | J2 | connector 10F | J3 |
| connector 10F | J4 | pot 3t 20K | R1 |
| resistor 4.7KΩ | R2 | resistor 2.2KΩ | R3 |
| resistor 10KΩ | R4 | resistor 10KΩ | R5 |
| pot 3t 10KΩ | R6 | pot 3t 10KΩ | R7 |

| Component/Element # | Ref. No. | Component/Element # | Ref. No. |
|---|---|---|---|
| resistor 4.7KΩ | R8 | resistor 4.7KΩ | R9 |
| resistor 100KΩ | R10 | resistor 22MΩ | R11 |
| resistor 10KΩ | R12 | resistor 220KΩ | R13 |
| resistor 14 dip 10KΩ | R14 | resistor 14 dip 10KΩ | R15 |
| resistor 10KΩ | R16 | resistor 14 dip 10KΩ | R17 |
| resistor 10Ω | R18 | resistor 10KΩ | R19 |
| resistor 10KΩ | R20 | resistor 10 sip val | R23 |
| pot 3t 10KΩ | R24 | resistor 10KΩ | R30 |
| resistor (used if different voltage) | R32 | 7 pin dip switch | S1 |
| 7 pin dip switch | S2 | test point | TP1 |
| test point | TP2 | test point | TP3 |
| dip14 LM339NA | U2 | dip 14 4066 | U4 |
| dip 8 LM555CNB | U5 | RX1300 | U6 |
| dip 16 74HC4060 | U7 | dip 16 74HC4040 | U8 |
| dip 16 74HC190 | U9 | dip 16 4511 | U10 |
| dip 16 74123 | U11 | dip 16 74HC190 | U12 |
| dip 16 4511 | U13 | dip 16 74HC190 | U14 |
| dip 16 4511 | U15 | dip 14 74HC08 | U16 |
| dip 8 LM386 | U17 | dip 14 4066B | U18 |
| dip 14 4066B | U19 | dip 14 74HC164 | U20 |
| dip 16 74HC160 | U21 | dip 16 4511 | U22 |
| dip 16 74HC190 | U23 | dip 16 4511 | U24 |
| dip 16 74HC190 | U25 | dip 16 4511 | U26 |
| dip 16 74HC160 | U28 | dip 16 74HC42 | U29 |
| dip 14 74HC04 | U30 | TO-220AB LM7805CTB + 5V reg | VR1 |
| TO-39 LM78L15ACZA + 15V reg | VR2 | XTAL crystal 32768 | X1 |

Of course, any other receiver unit can be used as well and any other circuit board design can be used as well provided that the receiver can receive a transmitted signal and generate a human cognizable response and optionally store, analyze and/or output information about each grinding episode such as duration, pressure amplitude and/or direction, time of occurrence, or the like.

Although the invention has been disclosed with reference to its preferred embodiments, from reading this description those of skill in the art may appreciate changes and modification that may be made which do not depart from the scope and spirit of the invention as described above and claimed hereafter.

We claim:

1. An apparatus to sense teeth grinding comprising:
    a. a mouth piece suitable to detachably engage teeth and a pallette of an upper jaw including:
        i. a socket designed to cover at least one tooth of the upper jaw;
        ii. a pressure sensor associated with the sockets, where the sensor produces a sensor signal when an activating pressure greater than a sensor threshold pressure is applied thereto;
        iii. a transmitter unit in electrical communication with the sensor designed to generate an action signal when a sensor signal having an amplitude greater than a sensor signal threshold amplitude is detected; and
    b. a receiver unit designed to receive the action signal and generate an human cognizable output.

2. The apparatus of claim 1, wherein the transmitter unit includes:
    a. a monitor designed to detect the sensor signal and to determine whether the amplitude of the sensor signal is greater than the threshold amplitude; and
    b. a transmitter designed to transmit the action signal.

3. The apparatus of claim 1, wherein the receiver unit includes:
  i. a receiver designed to receive the action signal; and
  ii. an output generator designed to generate an human cognizable output in response to the action signal.

4. The device of claim 3, wherein the receiver unit is part of the mouth piece.

5. The apparatus of claim 1, wherein the output is a vibratory output, an audible output, an electric output, a smell, a taste or a combination thereof.

6. An apparatus for protecting teeth comprising:
  a. a member suitable to detachably engage teeth and a pallette of an upper jaw including:
    i. a socket designed to receive the teeth of the upper jaw; and
    ii. a pressure sensor associated with a plurality of molar sockets, where each senor produces a sensor signal when an activating pressure greater than its sensor threshold pressure is applied thereto.

7. The apparatus of claim 6, further comprising:
  iii. a transmitter unit in electrical cmmunication with the sensor adapted to produce an action signal when an amplitude of the sensor signal is greater than a threshold sensor signal amplitude.

8. The apparatus of claim 7, wherein the transmitter unit includes:
  a) a monitor designed to detect the sensor signal and to determine whether the amplitude of the sensor signal is greater than the threshold amplitude; and
  b) a transmitter designed to generate the action signal.

9. The apparatus of claim 6, wherein further comprising:
  iv. an output generator designed to generate an human cognizable output in response to the action signal.

10. The apparatus of claim 6, wherein the output is a vibratory output, an audible output, an electric output, a smell, a taste or a combination thereof.

11. A method comprising the steps of:
  a. placing a mouth piece apparatus designed to detachably engage teeth and a pallette of an upper jaw in a wearer's mouth comprising:
    i. sockets designed to receive the teeth of the upper jaw;
    ii. a sensor associated with each socket, where the sensor produces a sensor signal when an activating pressure greater than a sensor threshold pressure is applied thereto;
    iii. a transmitter in electrical communication with the sensors designed to generate an action signal when a sensor signal having an amplitude greater than a sensor signal threshold amplitude is detected; and
  b. generating an human cognizable response to the action signal.

12. The method of claim 11, further comprising the step of:
  c. continuing the response until the action signal stops.

13. The method of claim 11, further comprising the step of:
  d. discontinuing the response when the action signal stops.

14. The method of claim 11, wherein the action signal is a start signal and the method further comprising:
  e. discontinuing the response when the action signal is a stop signal.

15. The method of claim 11, wherein the mouth piece apparatus further includes:
  iv. a receiver unit designed to receive the action signal and generate an human cognizable output in response thereto.

16. A method comprising the steps of:
  a. placing a mouth piece apparatus designed to detachably engage teeth and a pallette of an upper jaw of a wearer's mouth comprising:
    i. sockets designed to receive the teeth of the upper jaw;
    ii. a sensor associated with each socket, where the sensor produces a sensor signal when an activating pressure greater than a sensor threshold pressure is applied thereto;
    iii. a transmitter in electrical communication with the sensors designed to generate an action signal when a sensor signal having an amplitude greater than a sensor signal threshold amplitude is detected;
  b. receiving the action signal from the mouth piece; and
  c. storing information contained in the action signal.

17. The method of claim 16, further comprising the step of:
  d. analyzing the information stored in step (c).

18. The method of claim 17, further comprising the step of:
  e. generating an human cognizable response to the action signal.

19. The method of claim 18, wherein the information further includes a magnitude of a force or pressure associated with each grinding episode.

20. The method of claim 16, wherein the information includes a start, a stop and a duration of each grinding episode.

21. The method of claim 20, wherein the information further includes a direction of the force or pressure associated with each grinding episode.

22. A mouth guard comprising:
  a. a tooth portion designed to detachably engage teeth of the upper jaw including:
    i. sockets designed to receive each tooth of the upper jaw;
    ii. a pressure sensing membrane associated with at least each molar socket, where the membrane comprises a top conductive layer, a middle perforated layer and a bottom conductive layer, where the membrane has a rest state and an action state where the action state occurs when the top conductive layer is brought into electrical contact with the bottom conductive layer by the action of a pressure exerted between teeth on the upper jaw and teeth on a lower jaw greater than a membrane threshold pressure; and
  b. a pallette portion designed to detachably engage a pallette of the upper jaw including:
    i. a transmitter unit located in a central region of the pallette in electrical communication with the membrane, where the unit generates an action signal when the sensor signal has an amplitude greater than a sensor signal threshold amplitude.

23. The guard of claim 22, wherein the transmitter unit includes a transmitter for transmitting the action signal and a battery for supplying power to the guard.

24. The guard of claim 22, wherein the transmitter unit is field activated and includes a transmitter for transmitting the action signal and an antenna for absorbing power from a field to power the guard.

25. An apparatus for sensing teeth grinding comprising:
  a. a mouth guard comprising:
    i. a tooth portion designed to detachably engage teeth of the upper jaw including:
      a) sockets designed to receive each tooth of the upper jaw;

b) a pressure sensing membrane associated with at least each molar socket, where the membrane comprises a top conductive layer, a middle perforated layer and a bottom conductive layer, where the membrane has a rest state and an action state where the action state occurs when the top conductive layer is brought into electrical contact with the bottom conductive layer by the action of a pressure exerted between teeth on the upper jaw and teeth on a lower jaw greater than a membrane threshold pressure;

ii. a pallette portion designed to detachably engage a pallette of the upper jaw including:

a) a transmitter unit located in a central region of the pallette in electrical communication with the membrane, where the unit generates an action signal when the sensor signal has an amplitude greater than a sensor signal threshold amplitude; and b. a receiver unit designed to receive the action signal and generate an human cognizable output.

26. The apparatus of claim 25, wherein the transmitter unit includes a transmitter for transmitting the action signal and a battery for supply power to the guard.

27. The apparatus of claim 25, wherein the transmitter unit is field activated and includes a transmitter for transmitting the action signal and an antenna for absorbing power from a field to power the guard.

* * * * *